United States Patent
Luciano et al.

(10) Patent No.: US 12,186,141 B2
(45) Date of Patent: Jan. 7, 2025

(54) MEDICAL DEVICE STAND WITH INTEGRATED CLEANING CHAMBER

(71) Applicants: Vincent P. Luciano, Port Jefferson Station, NY (US); Ron Goldman, Cold Spring Harbor, NY (US)

(72) Inventors: Vincent P. Luciano, Port Jefferson Station, NY (US); Ron Goldman, Cold Spring Harbor, NY (US)

(*) Notice: Subject to any disclaimer, the term of this patent is extended or adjusted under 35 U.S.C. 154(b) by 456 days.

(21) Appl. No.: 17/803,231

(22) Filed: Mar. 21, 2022

(65) Prior Publication Data
US 2023/0310116 A1 Oct. 5, 2023

(51) Int. Cl.
| | |
|---|---|
| *A61B 90/70* | (2016.01) |
| *A61B 5/00* | (2006.01) |
| *A61B 90/00* | (2016.01) |
| *A61B 90/90* | (2016.01) |
| *F16M 11/42* | (2006.01) |

(52) U.S. Cl.
CPC .............. *A61B 90/70* (2016.02); *A61B 5/489* (2013.01); *A61B 90/90* (2016.02); *F16M 11/42* (2013.01); *A61B 90/36* (2016.02); *F16M 2200/066* (2013.01)

(58) Field of Classification Search
CPC ......... A61B 90/70; A61B 5/489; A61B 90/90; A61B 90/36; A61B 2562/24; A61B 5/0062; A61B 5/1171; A61B 5/6844; A61B 2560/045; F16M 11/42; F16M 2200/066; F16M 11/041; F16M 11/40
See application file for complete search history.

(56) References Cited

U.S. PATENT DOCUMENTS

| | | | | |
|---|---|---|---|---|
| 3,745,989 | A * | 7/1973 | Pinna .................... | A61B 5/0053 600/481 |
| 7,791,044 | B1 * | 9/2010 | Taylor ....................... | A61L 2/10 250/493.1 |
| 2010/0266445 | A1 * | 10/2010 | Campagna .............. | A61L 2/202 422/23 |
| 2016/0324997 | A1 * | 11/2016 | Dayton .................... | A61L 2/10 |
| 2017/0173200 | A1 * | 6/2017 | Wyman ................ | A47K 5/1217 |
| 2021/0308296 | A1 * | 10/2021 | Cook ................... | A47B 49/008 |
| 2021/0322594 | A1 * | 10/2021 | Ahmad ..................... | A61L 2/10 |
| 2021/0338863 | A1 * | 11/2021 | Hammad ................. | A61L 2/10 |
| 2022/0233731 | A1 * | 7/2022 | Chang ..................... | A61L 2/206 |
| 2022/0370673 | A1 * | 11/2022 | Ouni ........................ | A61L 2/10 |
| 2023/0241264 | A1 * | 8/2023 | Cao .......................... | C02F 1/32 250/455.11 |
| 2023/0310116 | A1 * | 10/2023 | Luciano ............... | F16M 11/041 |

* cited by examiner

*Primary Examiner* — David A Vanore

(57) ABSTRACT

A cleaning chamber for cleaning a vein viewing device, includes a housing with an access door having an open position and a shut position, wherein when the access door is in the open position the vein viewing device can be placed inside the housing. When the access door is in the closed position the housing and access door together envelop the vein viewing device. A detector detects when the vein viewing device is contained within the housing. A light source is contained within the housing and is arranged to illuminate the exterior surfaces of the vein viewing device when the vein viewing device is detected within the housing.

13 Claims, 29 Drawing Sheets

1401 — VEIN VIEWER STORED
- Stand 1200 positioned in hospital hallway
- Vein viewer 1201 in Chamber 1206
- Chamber 1206 plugged into power source
- Vein Viewer charging
- Front door 1303 shut
- Vein viewer 1201 cleaned
- Front door 1303 unlocked

1402 — UTILIZING THE VEIN VIEWER
- Unplug the Chamber 1206
- Roll the stand 1200 into a patient's room
- Remove the Vein Viewer 1201 from the Chamber 1206
- Use the Vein Viewer in a handheld mode to locate veins
- Place the vein viewer 1201 into the cup 1202 and manipulate the flexible arm 1203 to an appropriate position
- Perform procedure
- Place unit into cleaning chamber 1206 and shut front Door
- Front Door is locked

1403 — RETURN TO STORAGE LOCATION
- Roll the stand 1200 back to the hallway
- Plug the Chamber 1206 into the power source
- Cleaning cycle run
- Vein Viewer charging
- Front Door Unlocks

Fig. 15

MEDICAL DEVICE STAND WITH INTEGRATED CLEANING CHAMBER

CROSS REFERENCES TO RELATED APPLICATIONS

This application claims priority on U.S. Provisional Patent Application Ser. No. 63/206,046 having the title "Medical Device Stand with Integrated Cleaning Chamber," filed on Jan. 22, 2021.

FIELD OF THE INVENTION

The subject technology relates generally to a medical vein viewing device wherein the device is utilized with a medical device stand with an integrated cleaning chamber.

BACKGROUND OF THE INVENTION

Medical vein viewing devices are known in the art for detecting the position of a patient's veins and then displaying the patients vein pattern. Examples of such devices are the VivoLight Projection Vein Finder VIVO500S, the Christies Vein Viewer Flex, and the AccuVein AV500. The Vein Viewer Flex and the VIVO500S have user accessible wired ports for connecting the devices to an external device, such as a desktop or portable computer, for downloading of captured images of the veins, or in the case of the VIVO500S product, a removeable memory card can be removed and installed in a remote device to transfer the images. None of the existing vein viewing devices in the market incorporate radios for communicating with external devices. Embodiments are presented herein wherein radios are incorporated within the vein viewers.

Vein viewers are utilized in locations where they can possibly be stolen. For example, in hospital emergency rooms, patients and visitors often have access to the vein viewers, and given their pocketable size, they can be easily stolen. Still further, it is often desired to keep a vein viewer in a particular department. The small size makes it very easy for users from other departments to remove the units. Various embodiments are described for securing the vein viewers.

Hospitals are often very large, and it is difficult to locate within the facility a particular medical device such as a vein viewer. Various embodiments are presented wherein the vein viewer location is tracked, and actions are enabled or taken as a function of the location of the vein viewer.

Cleaning of medical device is of great importance within hospitals. The cleaning methodologies vary by hospitals, but often involves a spray and wipe technique consisting of applying a cleaning liquid to the equipment, allowing the liquid to remain on the equipment for 3 to 5 minutes, and then wiping the liquid off the equipment. This approach is not always effective given that the liquid might not be applied to all surfaces of the equipment, and therefore, the cleaning will only be partially completed. A further practical challenge is that this is a long procedure, and given the nurses busy schedules, they often do not have the time to properly clean the equipment, and often skip this cleaning step. Ignoring or bypassing the hospital's cleaning protocol can lead to increased infections within the hospital. Embodiments are presented wherein confirmation of the cleaning protocol is provided automatically. Further embodiments are shown where a UVC cleaning chamber is incorporated with the rolling stand.

Smartphones are very prevalent in hospitals. Embodiments are shown wherein vein viewer functionality is incorporated directly into the smartphone. Further embodiments are shown wherein a vein viewing attachment connects to the smartphone.

Vein viewers do not accurately detect the depth of the vasculature. Embodiments are shown wherein the time-of-flight of light reflected from the patient is calculated within a vein viewer and the depth of the vasculature is determined and subsequently displayed.

It is noted that the citing of any reference within this disclosure, i.e., any patents, published patent applications, and non-patent literature, is not an admission regarding a determination as to its availability as prior art with respect to the herein disclosed and claimed method/apparatus.

The herein disclosed apparatus provides improvements upon certain prior art vein viewing devices.

BRIEF DESCRIPTION OF THE DRAWINGS

FIG. 15 illustrates a flow diagram for the operation of a vein viewer device with a stand incorporating the UVC chamber.

DETAILED DESCRIPTION OF THE INVENTION

Figure 1:
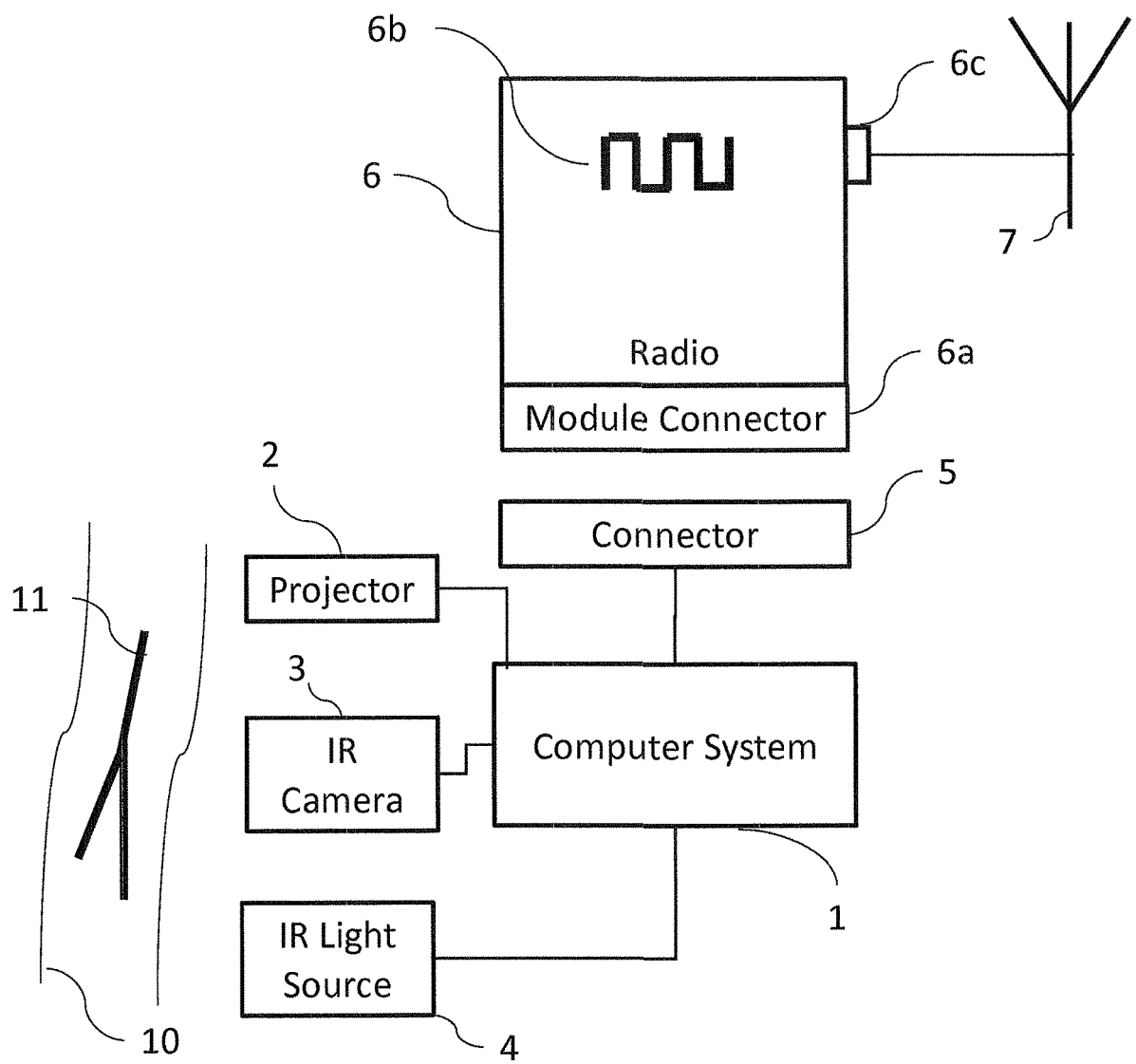
FIG. 1 illustrates a vein viewing device interfacing with a removable radio module.

As used throughout this specification, the word "may" is used in a permissive sense (i.e., meaning having the potential to, or being optional), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that the citing of any reference within this disclosure, i.e., any patents, published patent applications, and non-patent literature, is not an admission regarding a determination as to its availability as prior art with respect to the herein disclosed and claimed apparatus/method.

Furthermore, any reference made throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with design variations described in the specification, as well as applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Radio modules are available that comprise one or more of a WAR, WLAN, IRR or PAN radio transceiver. Such radio modules attached to a mobile device, thereby enabling wireless communications to and from such a device. An embodiment of the present invention is illustrated in FIG. 1. An IR light source 4 directs IR light at a patient 10, wherein the veins 11 of the patient absorb the IR light thereby reflecting an IR light pattern representative of the veins 11 towards an IR camera 3 which captures a representation of the patients 10 vein pattern 11. The camera 3 communicates the captured image to a computing system 1, which in turn processes the image to accentuate the vasculature and communicates the processed image to a projector 2 which projects in visible light, the image onto the patient 10. The camera 3 and the projector 2 are optically aligned so that they image and project at the same locations on the patient 10. In the present embodiment, the computing system 1 connects to an electrical and mechanical connector 5 which in turn connects to a mating radio module connector 6a of radio module 6. The radio module 6 can include antenna 6b printed on the module, and or, can have a remote antenna connector 6c for connecting to a remote antenna 7. An illustrative example of the radio module 6 is part number ATWINC3400-MR210CA from Microchip Technology Inc. This radio module is an IEEE 802.11 b/g/n RF/Baseband/Medium Access Control (MAC) network controller module with Bluetooth Low Energy technology that is compliant with Bluetooth version 4.0. This module is optimized for low power and high-performance mobile applications. This module features small form factor when integrating Power Amplifier (PA), Low-Noise Amplifier (LNA), Transmit/Receive (T/R) switch (for Wi-Fi® and Bluetooth), Power Management Unit (PMU), and Chip Antenna.

There are many industry standard radios 6 that can be incorporated into a vein viewer. Four general categories of radios are described below. When the term radio is used herein, it is not limited to the types of radios referenced herein, but refers to any radio capable of transmitting data to and from a vein viewing device.

Wide area radios (WAR), such as the types that are utilized in smart phones, are capable of transmitting voice and data over existing phone company infrastructure. Many different standards exist for wide area radio networks, including but not limited to, GMS, GPRS, CDMA, EDGE, UMTS, DECT, IS-136/TDMA. In an embodiment of the present invention, referring to FIG. 1, the radio 6 can be a wide area transceiver which is incorporated into a vein viewing device, thereby enabling the vein viewer to communicate data over the given wide area network. Wide area radios are advantaged in that there is no requirement for dedicated network infrastructure within the hospital or the location of the vein viewers. However, wide area radios can be disadvantaged, particularly in a hospital setting, where the device containing wide area radios are often prohibited from use due to potential interference with the hospital's sensitive medical instrumentation, and due to concerns regarding data privacy and security. Further, wide area radios consume more power than the WIFI and the PAN radios described below.

WIFI local area radio networks (WLAN) known as 802.11 networks are broadly deployed. The following are some of the various 802.11 protocols in existence (802.11a, 802.11b, 802.11g, 802.11-2007, 802.11n, 802.11-2012, 802.11ac, 802.11ad, 802.11af, 802.11-2016, 802.11ah, 802.11ai, 802.11aj, 802.11aq, 802.11ax, 802.11ay, 802.11ba, 802.11be). 802.11 transceivers can be placed in medical devices that enable transmission of data over the 802.11 network comprised of one or more access points. Such networks are deployed in most hospital and provide the ability to communicate data throughout the hospitals. Referring to FIG. 1, as an embodiment of the present invention, an 802.11 transceiver is incorporated into the radio 6 of a vein viewer thereby providing the ability to wireless communicate data throughout the location where the vein device is being utilized. Utilizing WIFI is advantageous in that the networks are often existing within a premise, eliminating the necessity of deploying new network infrastructure. However, many hospitals limit the access to the 802.11 network due to concerns about data security and patient safety.

Intermediate range radios (IRR), for example Amazon Sidewalk are typically used for Internet of Things (IOT) communication for controlling devices and exchanging limited data over distances in excess of the WLAN technology. This is often done by using a mesh network of WLAN and WPAN radios. As an embodiment of the present invention, referring to FIG. 1, an Amazon Sidewalk radio is incorporated as the radio 6 into a vein viewer thereby providing the ability to wireless communicate data throughout the location where the vein device is being utilized. Utilizing IRR is advantageous in that the networks can exist within a premise, such as a home, eliminating the necessity of deploying new network infrastructure. A public IRR is advantaged in that it would allow exchange of data such as arrival, procedure, procedure time and departure in a home healthcare setting when WLAN or WWAN are not available or are not desirable for reasons such as cost. IRR is often implemented as a software stack over a WLAN or PAN radio module and for the purposes of this disclosure PAN should be interpreted to cover both PAN and IRR applications.

Personal area networks (PAN) provide relatively short-range radio or infrared connectivity between devices. The Bluetooth protocol is an example of a PAN, however, there are many other alternatives available, such as but not limited, ZigBee, Bluetooth and ultrawideband. In the present invention, referring to FIG. 1, a PAN radio, such as for example, a Bluetooth transceiver is incorporated as a radio 6 into a vein viewer, thereby enabling communication with other Bluetooth enabled devices, such as, for example, a smartphone or portable computer.

Figure 2:
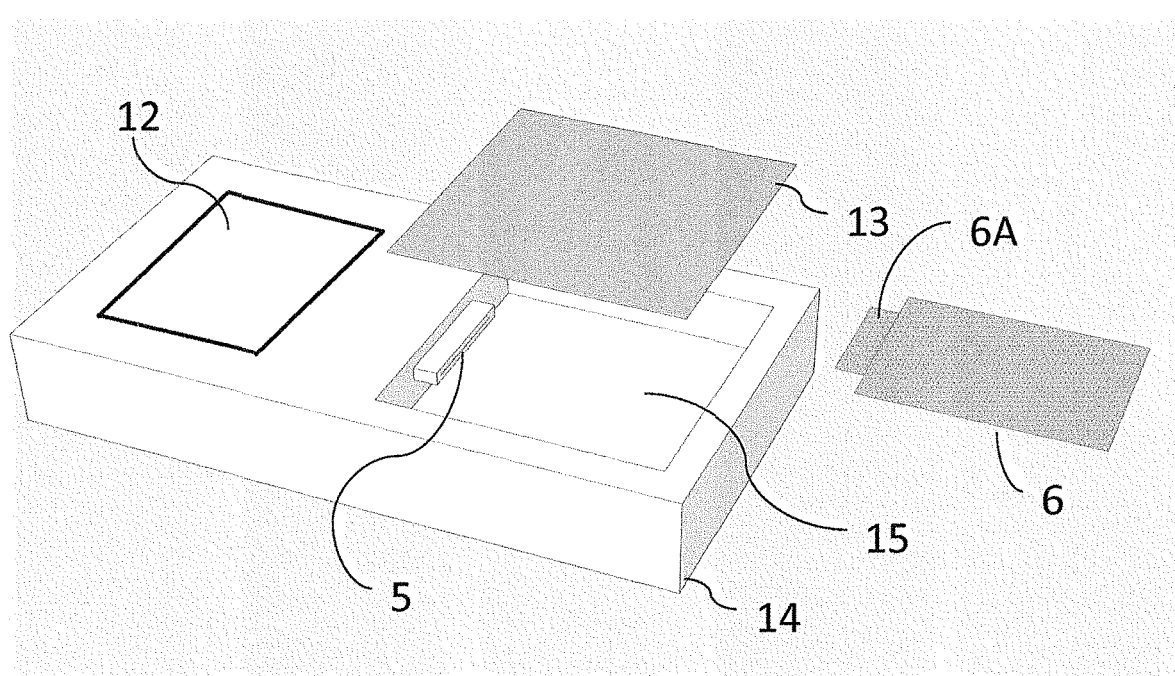
FIG. 2 illustrates the housing of a vein viewing device having a cavity to receive the radio module.

FIG. 2 is an illustration of a vein viewer housing 14 having a user accessible cavity 15 for housing the radio module 6. The computing system 1 and the connector 5 are mounted or connected to a main PCB 12. The radio module includes a connector 6a. To install the radio module 6, a cavity door 13 is removed by a user, and the radio module connector 6a is electrically and mechanically attached to the connector 5. After the radio module 6 is installed, the cavity door 13 can be reinstalled thereby enclosing the cavity 15 and protect the radio module 6 from moisture and dust.

Alternatively, the radio module 6 can be permanently affixed within the body of a vein viewer. In such a case, the connector 5 and radio module connector 6a can be affixed so that the user cannot access or remove the radio module 6. In such a case there is no necessity for a user accessible cavity within the product to house the radio module 6. Still further, in such an embodiment, the connector 5 and the radio module connector 6a can be eliminated and the radio module 6 can be permanently affixed to the main PCB 12 via soldering or other method of providing electrical and mechanical connectivity.

Figure 3:
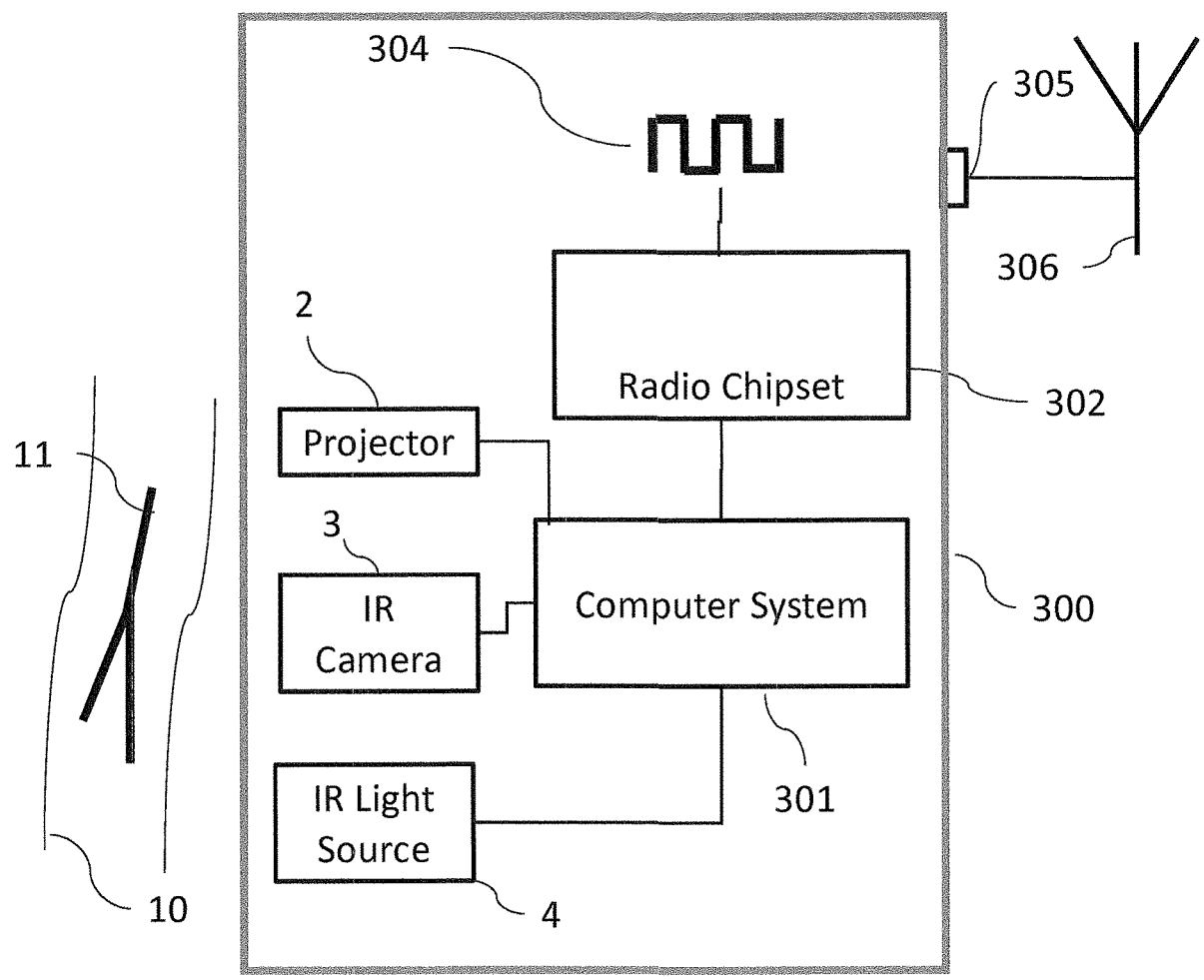
FIG. 3 illustrates a vein viewing device with an integrated radio chipset.

The radio functionality can be achieved by directly incorporating a radio chipset directly into the vein viewing product. As an embodiment, FIG. 3 illustrates mounting a radio chipset 302 directly onto a PCB 300 that incorporates the computing system 301. The computing system 301 electrically communicates with the radio chipset 302. The BCM43012 chipset from BroadCom is a representative example of a radio chipset 302 that can be utilize, however, there are many other radio chipsets that can be utilized. The antenna 304 can be mounted directly to the PCB 300 or can be simply the traces of the PCB laid out in an appropriate pattern. An external antenna 306 can be utilized by connection to antenna connector 305. The computer system 301 communicates with the projector 2, the IR camera 3 and the IR light source 4 as previously described with reference to FIG. 1 to effect the vein visualization.

Figure 4:
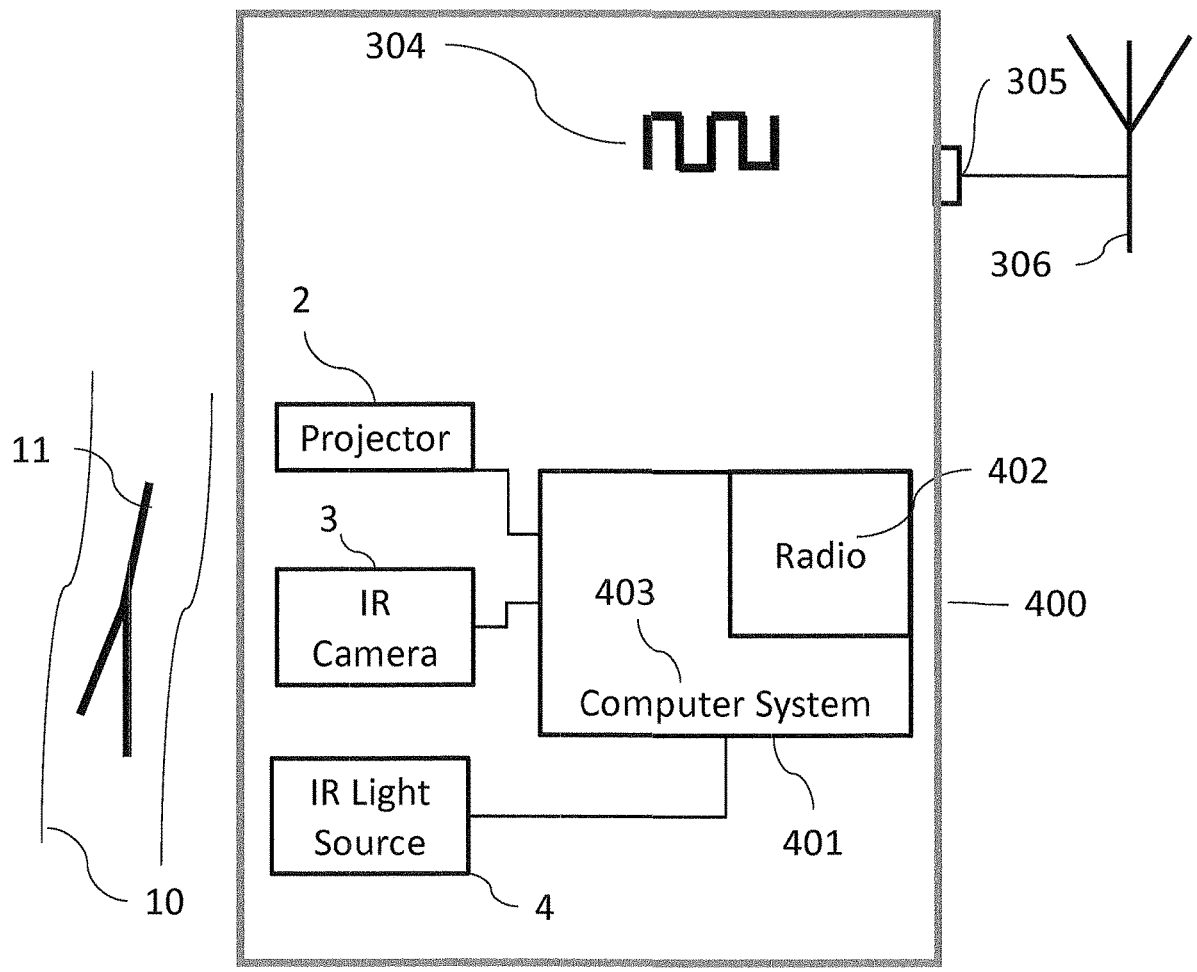
FIG. 4 illustrates a vein viewing device having a computer system with integrated radio functionality.

FIG. 4 illustrates an embodiment wherein a PCB 400 of the vein viewer incorporates a system on a chip 401 which in turn incorporates the computer system 403 together with the radio section 402 on a single chip or chipset 401. The radio can connect to an antenna 304 directly attached to the PCB 400, or can connect via remote connector 305 to and external antenna 306. The QualCom QCA4020 SoC is an illustrative example of a multi-mode system-on-chip with for dual-band Wi-Fi, Bluetooth 5 and 802.15.4-based technologies, including ZigBee and Thread. The computer system 403 communicates with the projector 2, the IR camera 3 and the IR light source 4 as previously described with reference to FIG. 1 to effect the vein visualization. The computer system also communicates with the radio section 402 to effectively send and receive data.

Figure 5A:
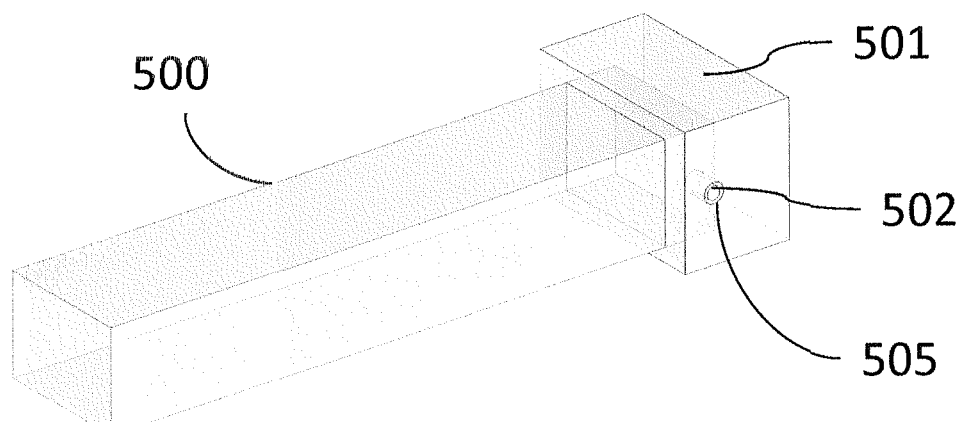
FIG. 5A illustrates a vein viewing device with a locking mechanism for securing the device into a receiving cup.

Theft of handheld and portable devices, such as, for example, a vein visualization device from a hospital, or other location of use, is of concern to users of such devices. FIG. 5A illustrates an embodiment wherein a vein viewing device 500 can be locked into place in a receiving cup 501. The receiving cup 501 can be permanently affixed to a larger or immovable object. A locking plunger 502 is incorporated into a vein viewing device 500. The locking plunger 502 can comprise a solenoid that when electrically activated withdraws the plunger 502 to within the outer profile of the vein viewing device 500. When electrical energy is removed from the solenoid, the plunger 502 moves to a position wherein it protrudes from the device 500. Fig. The cup 501 and the device 500 can be mutually shaped so that there is only one correct position (orientation) for the device 500 to be inserted into the cup 501. When the device 500 is inserted fully into the cup 501, the plunger 502 lines up with a cavity 505 in the receiving cup 501. While the device 500 is inserted into the receiving cup 501, and the plunger 502 is deactivated (in the protruding position), the plunger 502 is positioned within the cavity 505, thereby preventing the device 500 from being removed from the cup receiving 501. When in this state, assuming the receiving cup 501 is permanently affixed to a larger item, such as a desk or hospital bed, the device is protected from theft in that someone would have to steal the entire device 500 together with the larger item. Given that the larger item is relatively large, such a theft would be unlikely. To remove the device, the device 500 provides electrical energy to the solenoid which in turn retracts the plunger 502 into the device 500, and therefore the plunger is out of the cavity 505, thereby freeing the device 500 to be removed from the cup 501.

Figure 5B:
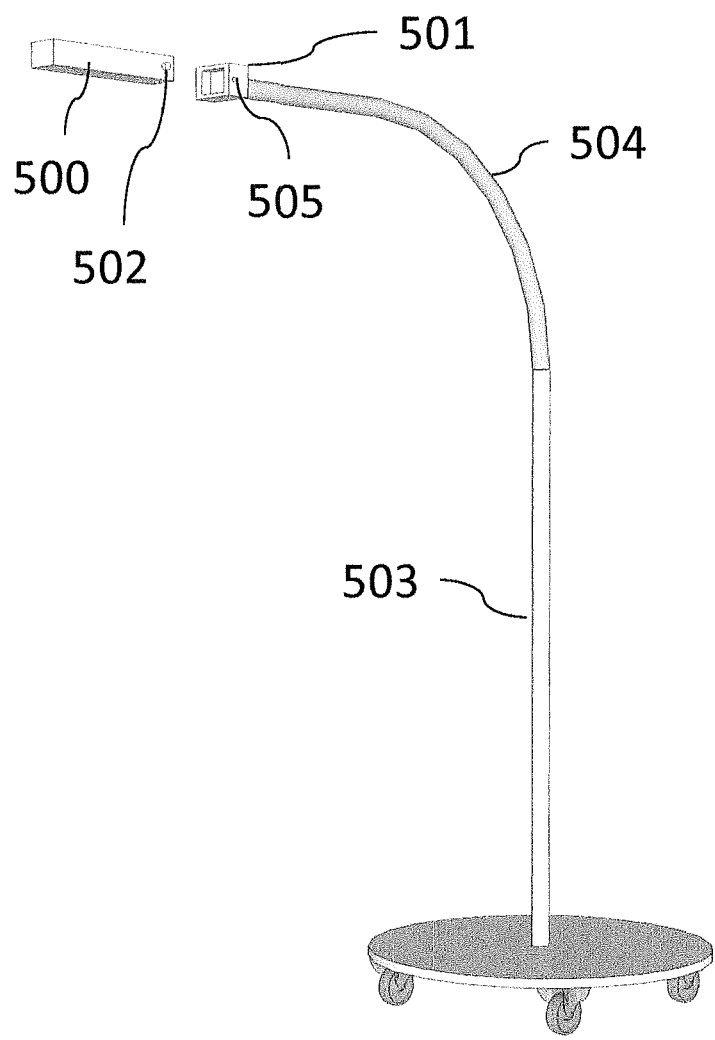
FIG. 5B illustrates the device and receiving cup of FIG. 5A mounted on rolling stand.

FIG. 5B illustrates an embodiment wherein the device 500 and the receiving cup of FIG. 5A is mounting onto a rolling stand 503. The rolling stand includes an articulating arm 504 which is securely attached to the receiving cup 501. When the device 500 is placed into the receiving cup 501, and the plunger 502 is extended into the cavity 505, the device cannot be removed from the stand, and therefore, in order to steal the device 500, the entire rolling stand 503 would have to be also stolen. Given the large size of the stand 503, such theft is unlikely.

Figure 5C:
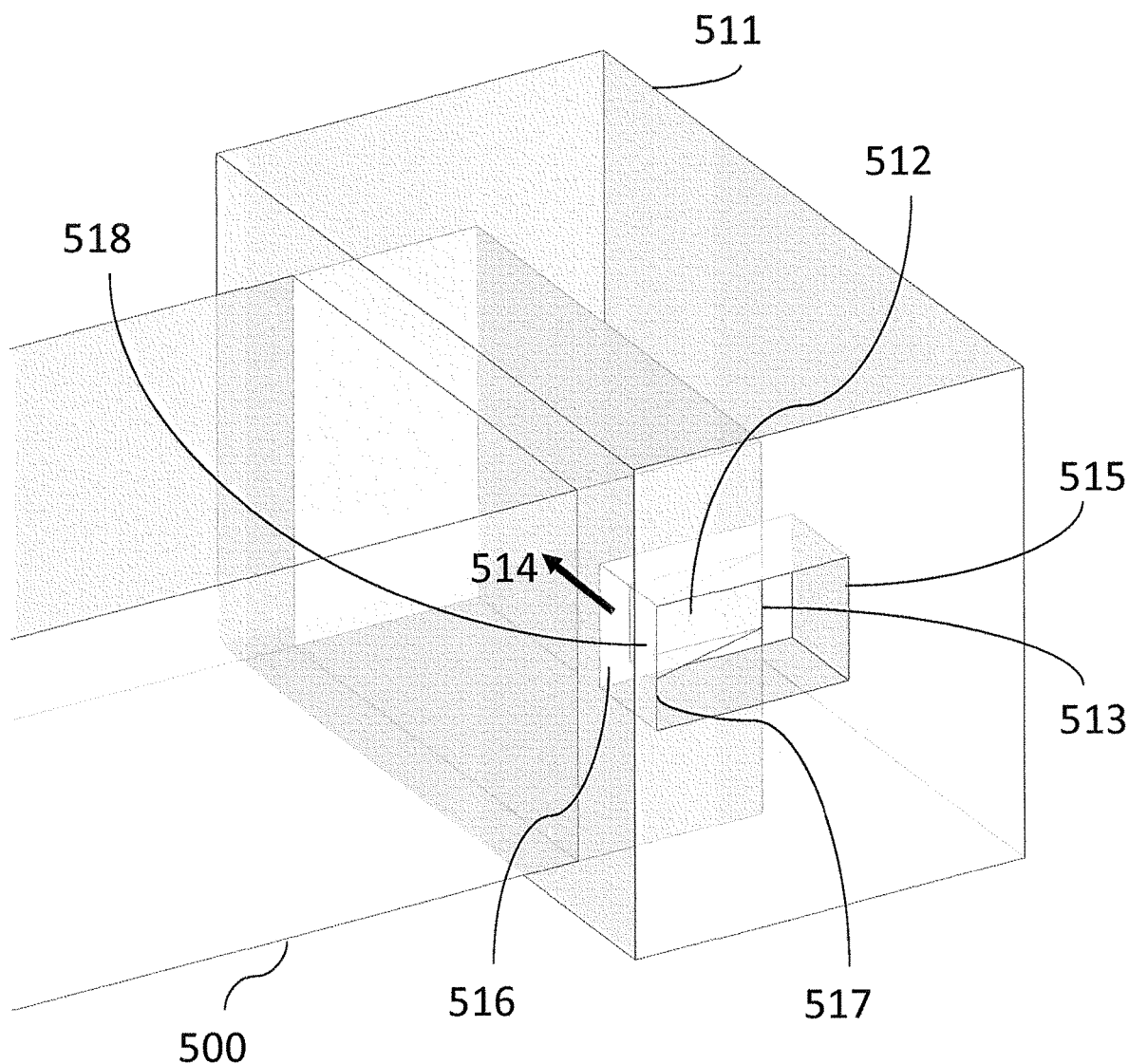
FIG. 5C illustrates a further embodiment of a locking mechanism for securely locking a vein viewing device to a receiving cup.

As a further embodiment, FIG. 5C illustrates an embodiment wherein the vein viewing device 500 can be inserted into cup 511 even while the plunger 512 is deenergized and protruding from the device 500. In this case the plunger 512 is triangularly shaped and pivots about pivot point 513. The plunger can be mechanically moved to its energized position (wherein the plunger 512 pivots about pivot point 513 and is flush with the vein viewing device 500) even without energy being supplied to the solenoid of the plunger 512, by pressing the plunger 512 in the direction 514 towards the body of the device. When the mechanical pressure is released and no energy is applied, the plunger 512 is arranged to return to its protruding state. Accordingly, as the device 500 is inserted into the cup 511, the wall 516 of the cup 511 applies mechanical pressure to the plunger 512 eventually pushing it so as to be flush with the surface of the device 500. As soon as the device 500 is pushed far enough into the cup 511 that the locking edge 518 of the plunger 512 moves past the locking edge of the cavity 517, the mechanical pressure is relieved and the plunger 512 moves to its non-energized locking position. Accordingly, at this point the device 510 cannot be removed from the cup, and is therefore theft proofed, until the plunger 512 is electrically activated and moved to a position wherein it is flush with the surface of the device 500.

Figure 6:
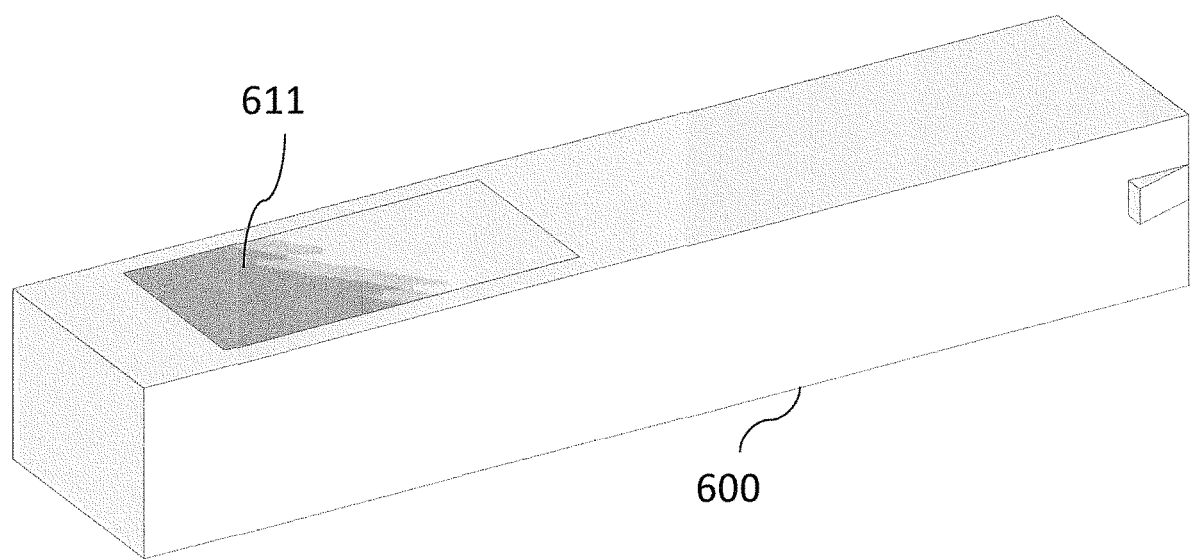
FIG. 6 illustrates a vein viewing device with a display.

The embodiments of FIGS. 5A, 5B and 5C require unlock signals generated by, or provide to, the device 500. An embodiment is shown in FIG. 6, wherein the vein viewing device 600, such as vein viewer 500 previously described in reference to FIG. 1, has a touch screen display 611 which enables the user to enter data into the device 600. In this case, the device can be programmed to unlock only when a predetermined code sequence is entered at the touch screen. Alternative, the device could have multiple unlock codes, each assigned to a different user. When a correct unlock code is entered, the device 600 can communicate to a remote device via the radio, the name of the user who unlocked the device and an appropriate date/time stamp record. When the device is returned to the cup and subsequently locked, the radio can communicate that the device has been returned to its cup. If a device fails to be returned, the last know user can be identified based upon the previous received radio data communications.

As an alternative to a touchscreen 611, any other type of known user input can be utilized, such as, key entry, scroll wheels, voice detection input, biometrics such as fingerprint or facial recognition. Further, the device could be configured to contain a RFID reader, and the unlock signal be generated upon detection of an appropriate RFID tag (a RFID key) being brought close to the unit.

Referring back to FIG. 1, the device contains an IR light source 4 and an IR camera 3 and a computing system 1 which can be configured to read bar codes or other optical indicia. Bar code reading algorithms are well known to those skilled in the art. An illustrative bar code algorithm that is available under license to incorporate into camera-based systems is distributed by a company called Anyline, and is hereby incorporated by reference. Accordingly, in a further embodiment, the device 600 of FIG. 6 can be configured to read barcodes or other optical indicia. The device can be programmed to unlock the device 600 only upon reading a predetermined barcode or predetermined optical pattern. Each user, or department, or any other useful segmentation of users, could be assigned different unique barcodes to unlock the device 600, and the radio within the device 600 could communicate each time a user unlocks a system.

An alternative unlocking trigger could be detecting the unique biometric pattern of the vasculature of each user. For example, the vein pattern on the back of the hand of each user is unique. This vein pattern, or a mathematical representation of the vein pattern, for each potential user could be stored in the device. To unlock the device, a user simply scans the back of their hand and their vascular pattern is capture and compared to those stored in the device. If there is an appropriate match, the device is unlocked, and a date and timestamped log of the unlocking user can be stored locally in the device or can be communicated in real time over the radio.

In another embodiment, the vasculature of the potential users can be stored in a remote computer. When a user scans their vasculature in an attempt to unlock the device, the vascular pattern captured is communicated by the device over the radio to the remote computer, which in turn, determines whether the user's pattern matches that contained in the computer's database. If it matches, a radio signal is sent to the device authorizing it to unlock the device, and the remote computer stores the user and date/time unlock information.

A smartphone with a radio (WAN, LAN or PAN) could be configured to communicate with a vein viewing device which includes a radio transceiver. The smartphone could have an application on it which determines when a user can unlock a device. There are many existing security methodologies already existing on smartphones for determining a user's credentials and authenticity. Pass codes, fingerprint, facial recognition, and voice recognition are all commonly used for authenticating a user. Once the smartphone application determines it is appropriate for a user to use the vein viewing device, a radio message is communicated to the device triggering the unlock.

It is known to place a location tracking device (or utilize the existing radio signals from a device) on a medical device for determining their physical position within a hospital. Such location information could be logically tied to the unlocking of a vein viewing device. For example, the location tracking system could determine that the devices can be unlock while they are in the surgical area (where theft probability is low), but could not be unlocked in the emergency room where the is a lot of uncontrolled access and therefore has a higher probability of theft. In one embodiment, the logic and the tracking information could all reside on the vein viewing device, and the appropriate unlocking and locking decisions be determined solely by the device. In an alternative embodiment, the vein viewing device can be unaware of its own location or of the locking and unlocking logic. A remote computer system can contain the real time location of the vein viewing devices, as well as the appropriate locations for unlocking (essentially geofencing). Upon determining that a unit can be unlocked, a radio signal is sent to that particular vein view device which then unlocks itself. This geofencing can be combined with the previously describe access by user for even more advance logic applied to unlocking.

Figure 7A:
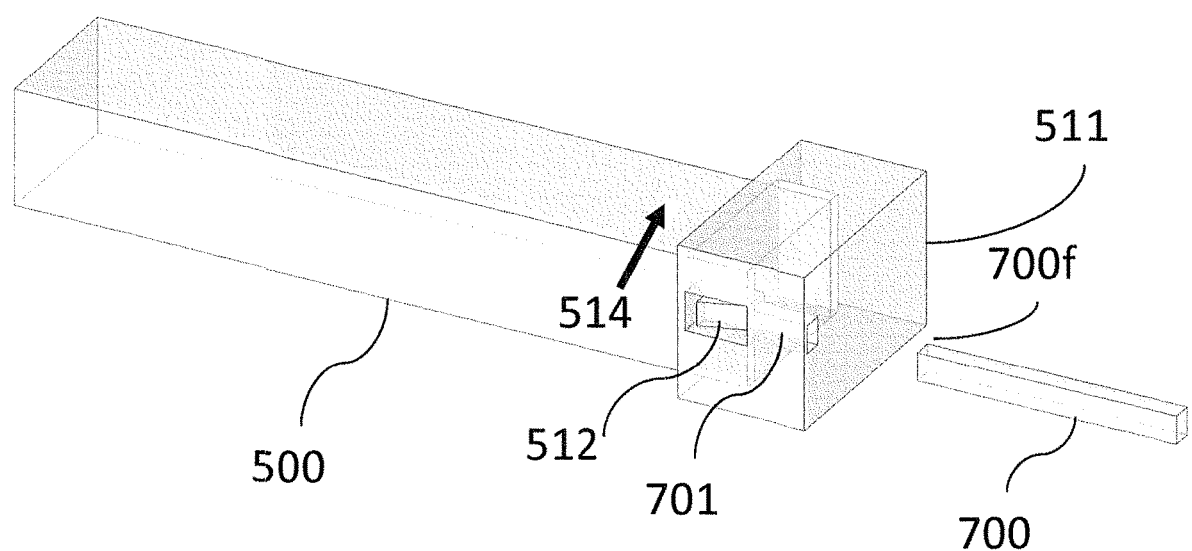
FIG. 7A is a ray trace illustration of a vein viewer locking mechanism with a mechanical unlock key.
Figure 7B:
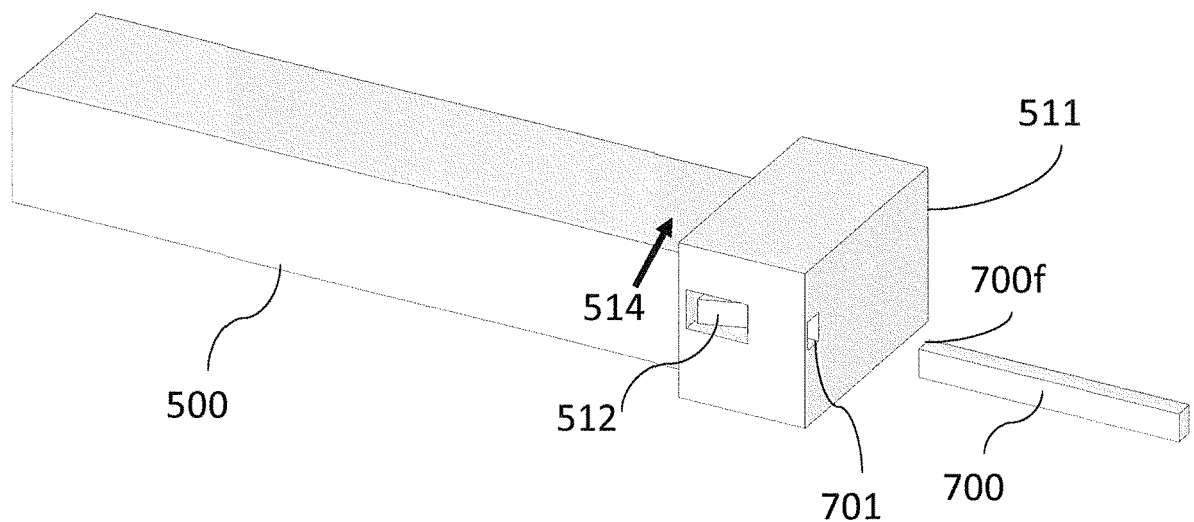
FIG. 7B is a solid view illustrating the vein viewer locking mechanism with a mechanical unlock key of FIG. 7A.

If the device fails to operate, due to electrical or mechanical failure, battery failure or other failure mechanisms, a situation could arise that the device is locked into a cup without being able to energize the plunger to unlock the unit. The embodiment shown in FIGS. 7A and 7B shows the FIG. 5C embodiment with the additional of a mechanical key 700 mechanism that can be utilized to unlock the unit. FIG. 7A is a ray trace view and FIG. 7B is a solid view. As a practical matter, a hospital might decide only to provide this key 700 to the biomedical department or to appropriate supervisors. The mechanical unlock key 700 is uniquely shaped to fit through a cutout 701 in the bottom of the cup 511. When the mechanical key 700 is fully inserted into the cutout 701 the front edge of the key 700*f* pushes the plunger 512 in direction 514 towards the unlocked position. The device can then be removed from the cup. The key can be made of a flexible material, and the cutout can be curved, to prevent a user from using a straight object to mechanically move the plunger to the unlock position. Other mechanical methods could be envisioned for unlocking the system provided an appropriate tool is available. For example, an external magnetic device could be utilized that moves the plunger to an unlocked position when appropriately positions.

When establishing unlocking criteria for a vein viewing device, a secure programming mode must be established in which the unlocking criteria is entered and stored. As previously described in reference to FIG. 6, the unlock criteria could be any input that is unknow or unavailable to a potential thief, or any user not authorized to unlock the system. Keypad inputs, barcodes and optical indicia, RFID, hardware keys, and biometric inputs are examples of potential unlock criteria that can also be utilized as a "master key" to place the vein viewing device into what will be referred to as a programming mode.

The device can come from the factory preconfigured with a "master key" that enables the device to be placed into a programming mode. Generally, in a hospital, this master key will be provided only to the biomedical department, or department supervisors, who then enroll the permitted users of the vein viewing device. In the case where the vein viewer device has a touch screen or keys, the master key can be a 4 digit sequence of numbers. This 4 digit sequence of numbers can be mathematically derived by the manufacturer based upon the products unique number. Accordingly, if the master key is lost by the hospital, it can be recovered based upon the serial number or other code assigned to the device. Alternatively, where the device is configured to read barcodes, or other optical indicia, a unique barcode can be provided with each vein viewing device. When unique bar code is read by the vein viewing device, the device enters the programming mode. A further method of entering a programming mode can be to utilize a unique hardware key, such as, a removeable micro SD card having predetermined data, that is inserted into the device, and upon detection of the predetermined data, the device enters the programming mode. Still further, a button or other user initiated trigger can be positioned in the unit where it is not easily accessible. For example, the button can be housed inside the battery cavity, in which case the user would need to remove or open the battery door to access the button. The access to the battery door can be guarded by utilizing a locking screw (a screw requiring a unique type driver to turn) or can be protected by a physical lock and key system. Still further, the user-initiated trigger can be a magnetic sensor within the product that detects the presence of a magnet when the magnet is placed in a predetermined position on the product. Such a magnetic sensor can be a hall effect device.

It might be desirable to utilize a remote device, such as a Bluetooth connected smartphone, as a programming device for entering in the unlock criteria, and then downloading by radio the information to enable the vein viewing device. In this manner, the high-resolution touchscreen of such smartphone can be utilized by applications programmed into the smartphone, to guide the entry of the unlock criteria.

Figure 8A:
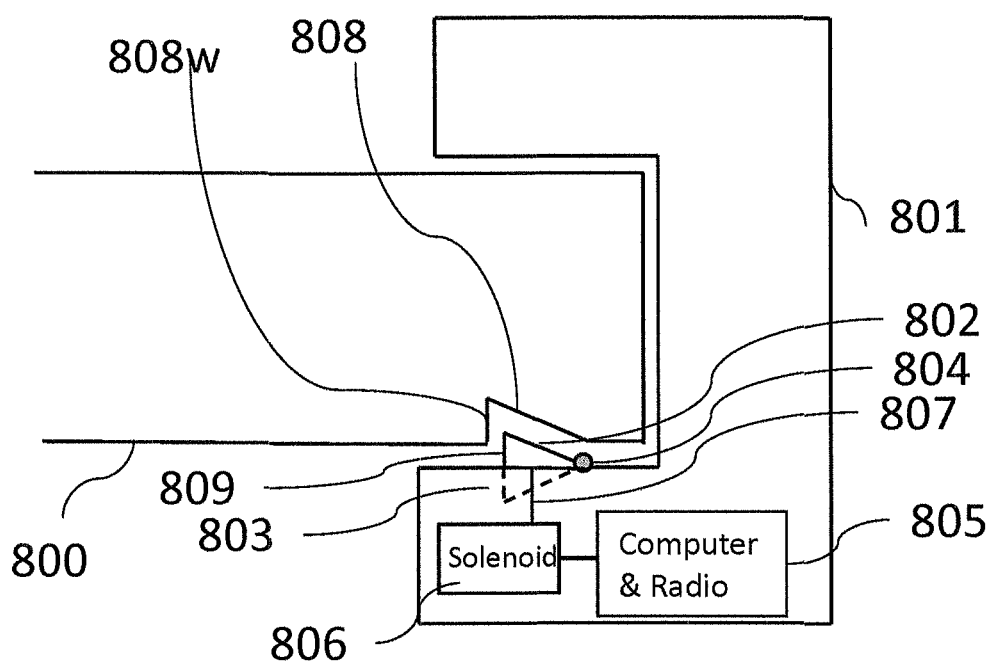
FIG. 8A illustrates utilizing a solenoid connected to a computer and radio to activate a locking mechanism for securely attaching a vein viewer device to a receiving cup.

FIG. 8A illustrates an embodiment wherein the locking plunger 802 is housed in the cup 801. The locking plunger 802 is mechanically connected to an actuating arm 807 which in turn is mechanically moved by an electrically actuated solenoid 806. The locking plunger 802 pivots about pivot point 804. When the solenoid 806 is not electrically activated, the locking plunger 802 protrudes from the interior wall of the cup 801. The vein viewing device 800 has a notch 808 shaped to receive the locking plunger 802, wherein the wall 808*w* of the notch 802 prevents the device 800 from being removed when the locking plunger is protruding into the notch 808. When the solenoid 806 is electrically activated, the locking plunger moves to be positioned 803 within the cup 801, and therefore the device 800 is freed to be removed from the cup 801.

The cup 801 has a system-on-chip 805, such as previously described in reference to FIG. 4, which enables it to communicate with a radio in the device 800. In this embodiment, a system-on-chip 805, contains the computing logic and the radio transceivers. The system-on-chip 805 communicates an electric signal (could be through intervening amplifiers) to the solenoid 806 to affect the locking and unlocking action. The device 800 can be utilized for determining the logic as to when to lock or unlock the device and can communicate such instructions via the radio to the cup 801. Alternatively, any radio enabled device in radio communications with the cup 801, could send the instructions to the cup to lock or unlock the device 800. It is possible in this embodiment to have electrical connections (not shown) between the device 800 and the cup 810 for providing power from the device 800 to the cup 801, wherein the power to the cup 801 to run the electronics 805 and the solenoid 806 is provided by the device 800 through the connectors.

Figure 8B:
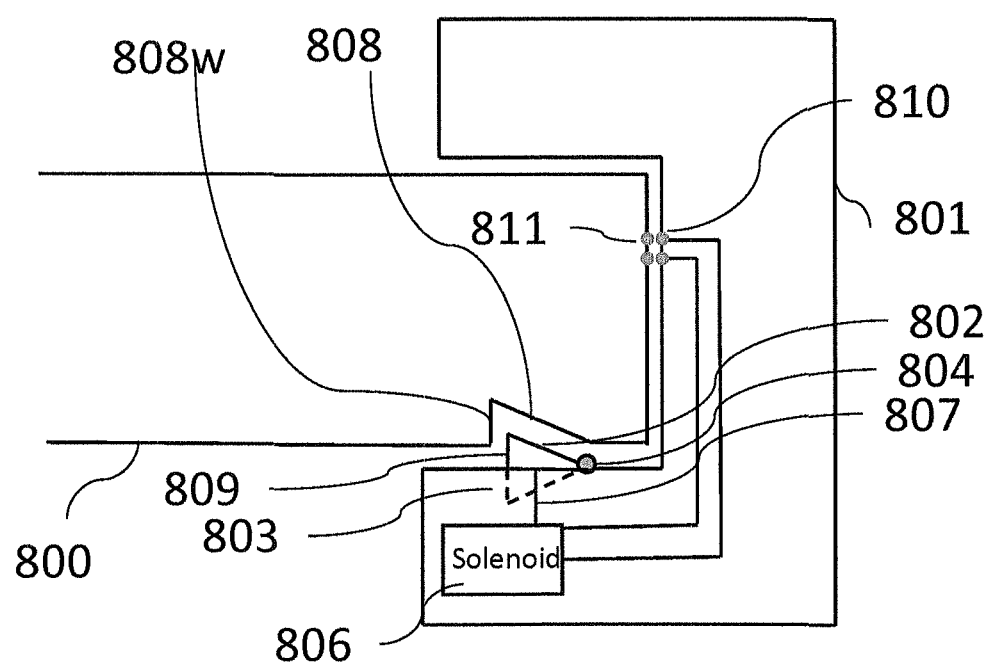
FIG. 8B illustrates a solenoid driven by the vein viewer device for securely attaching a vein viewer device to a receiving cup.

In a still further embodiment shown in FIG. 8B, the cup 801 can comprise a solenoid 806 that electrically connects directly to an electrical cup connector 810 on the cup 801, which in turn is electrically connected to an electrical device connector 811. The device 800 has electrically controlled amplifiers that can drive the signals to sufficient levels to activate and deactivate the solenoid 806. Accordingly, in this embodiment, the cup 801 does not need to be provided its own power to run electronics or to activate the solenoid 806.

While all the embodiments described show locking a device and a cup together, the invention it is not intended to be so limited. The cup can replace by any object that is fixed in place thereby minimizing theft, or is large enough, or heavy enough, or visible enough, to deter a thief from removing the device from the location of use. For example, the cup can be a wall mounted holder for the device, or the cup can be permanently affixed to a bed or phlebotomy chair. Alternatively, the cup can be a charging cradle, or an array of charging cradles designed to hold and charge the devices. While a particular locking mechanism has been illustrated, the present invention contemplates any locking mechanism, including, for example, magnetic locking systems, or alternative locking plunger shapes. Further, a solenoid has been utilized for actuating the locking mechanism, however, alternative actuating means may be employed, such as, for example, electrical, magnetic and mechanical locking mechanisms.

While the previous embodiments described a physical locking mechanism, and approaches to locking and unlock the device from a cup, a virtual locking mechanism can be employed. In this case, instead of locking the device physically, the device is placed into a mode where it does not function to display veins. Accordingly, the device is worthless to a thief given that it will not function to show veins. The device can then be unlocked by appropriate users utilizing the technique described herein, which in this case will involve enabling the unit to function to show the veins. The device can automatically enter into the virtual locked state after each use, or after a fixed time duration, or upon a predetermined schedule.

Depending on the devices lock state, a message can be displayed on the screen or an LED or other visible or audible indicator can show that the device is locked as a further deterrent. A motion detector could be optionally used such that when a locked device is handled an audible or spoken warning could be presented that the device is in a locked state.

Figure 9A:
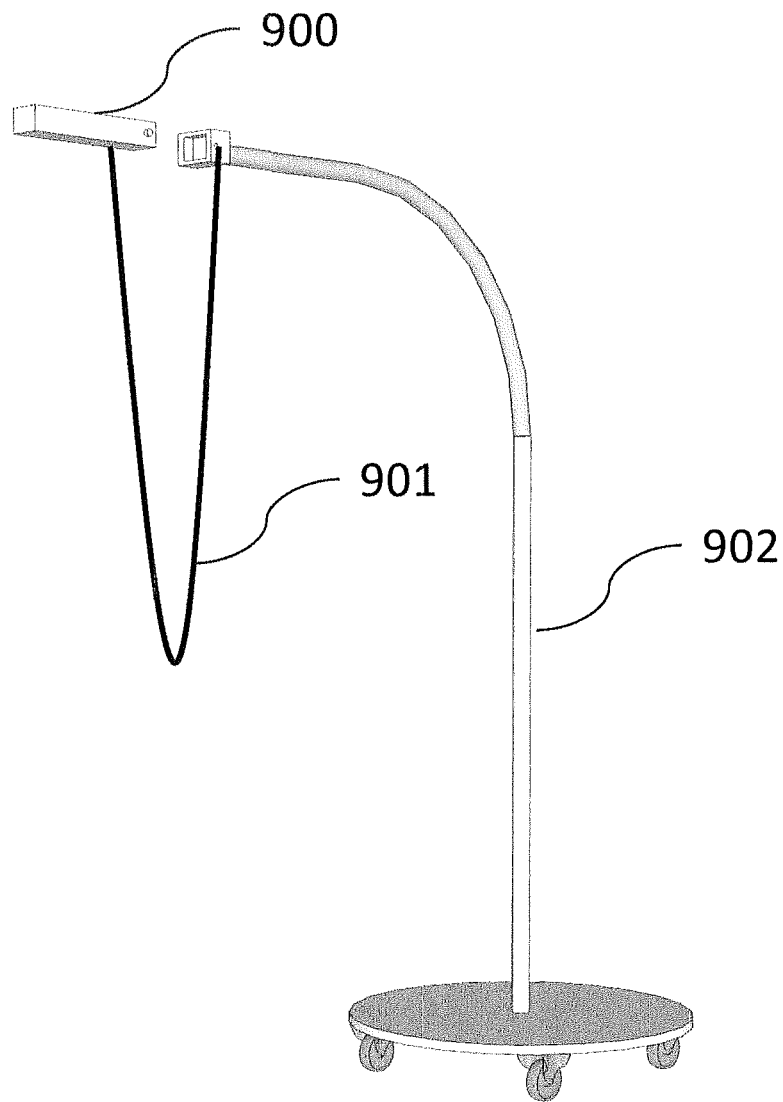
FIG. 9A illustrates a rolling stand with a physical tether.

It is a desirable feature to ensure that the device is not decoupled or taken to far a distance from the stand. This will help prevent theft or protect the device from being removed from a desired location. This is of particular concern in hospitals wherein departments often purchase equipment solely for use in their departmental locations. The portable aspect of the device makes it easy for someone from another department to knowingly, or inadvertently, move the device to another location. FIG. 9A shows one method of preventing this by utilizing a cable 901 attached to both the device 900 and the stand 902 to mechanically ensure the device 900 is not moved away from the stand 902. While this approach works from a security perspective, the cable 901 is very burdensome when attempting to use the device 900 in a handheld mode.

Figure 9B:
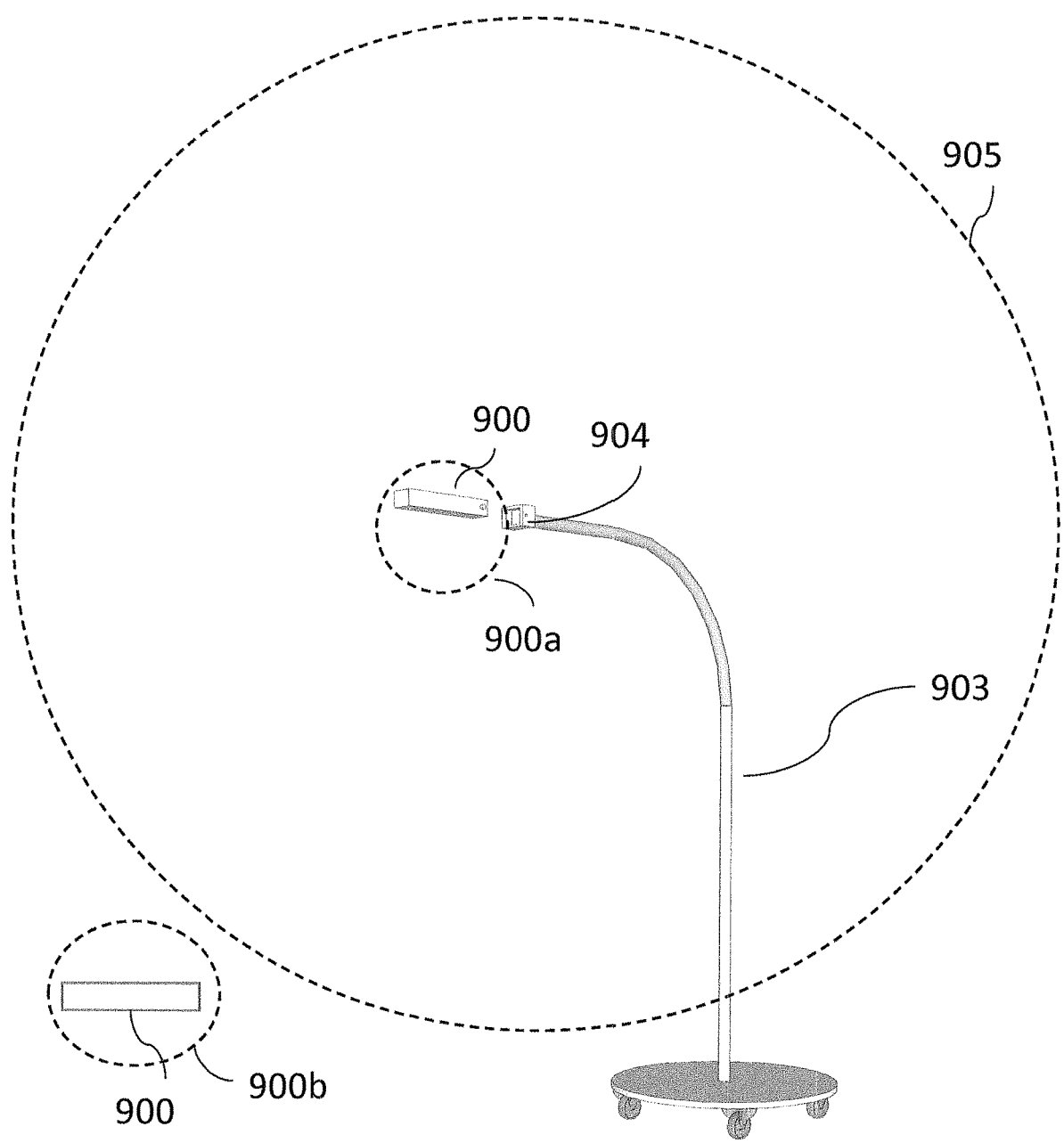
FIG. 9B illustrates a rolling stand with a radio tether.

An alternative embodiment is shown in FIG. 9B. In this embodiment short range radios, such as Bluetooth radios, are incorporated in both the vein viewing device 900 and cup 904. The receive and transmit power levels of the radio incorporated in the cup can be set so that the communication distance between the device 900 and cup 904 is limited to distance 905. When the device 900 is placed closer to the cup 904 (shown as for example position 904) than the distance 905, radio communications is detected between the device 900 and the cup 904, and the unit operates in a normal fashion. However, when the device 900 is moved to position 900b, which is outside of the radio distance 905, no radio communications are detected, and the device initiates an out-of-range warning sequence. The out-of-range warnings sequence can be sounds emitted from either the device 900, the cup 904, or both. Alternatively, the out-of-range warnings sequence can be visible indications on the device 900 and/or the cup 904. Still further, in response to an out-of-range warning, the device 900 can disable vein viewing functions until the device is brought back within range. Alternatively, in instances where the device 900 communications via radio to other devices or systems, out-of-range signals can be transmitted over the radio to remote devices or systems, and appropriate actions taken on the remote devices.

While this tethering has been illustrated using a Bluetooth radio, the invention is not limited thereto. Any type of radio scheme can be utilized. Alternative, optical transmission means can be utilized, such as, for example, IR transmitters such as the type utilized for TV remote controls. Still further, magnets can be utilized, wherein detection of the magnetic field below a certain threshold initiates the out-of-range sequence. Still further, RFID tags can be used wherein loss of detection of the tag initiates the out-of-range sequence.

Out of range warnings can also be sent out over a network, if that connection is available, such that any number of notification mechanisms such as email, text message or other alerts to a user's or administrator's device is made.

Various approaches can be used for determining the location of the vein viewing devices within a premise, such as a hospital. The device location information can be utilized in many beneficial ways.

Figure 10:
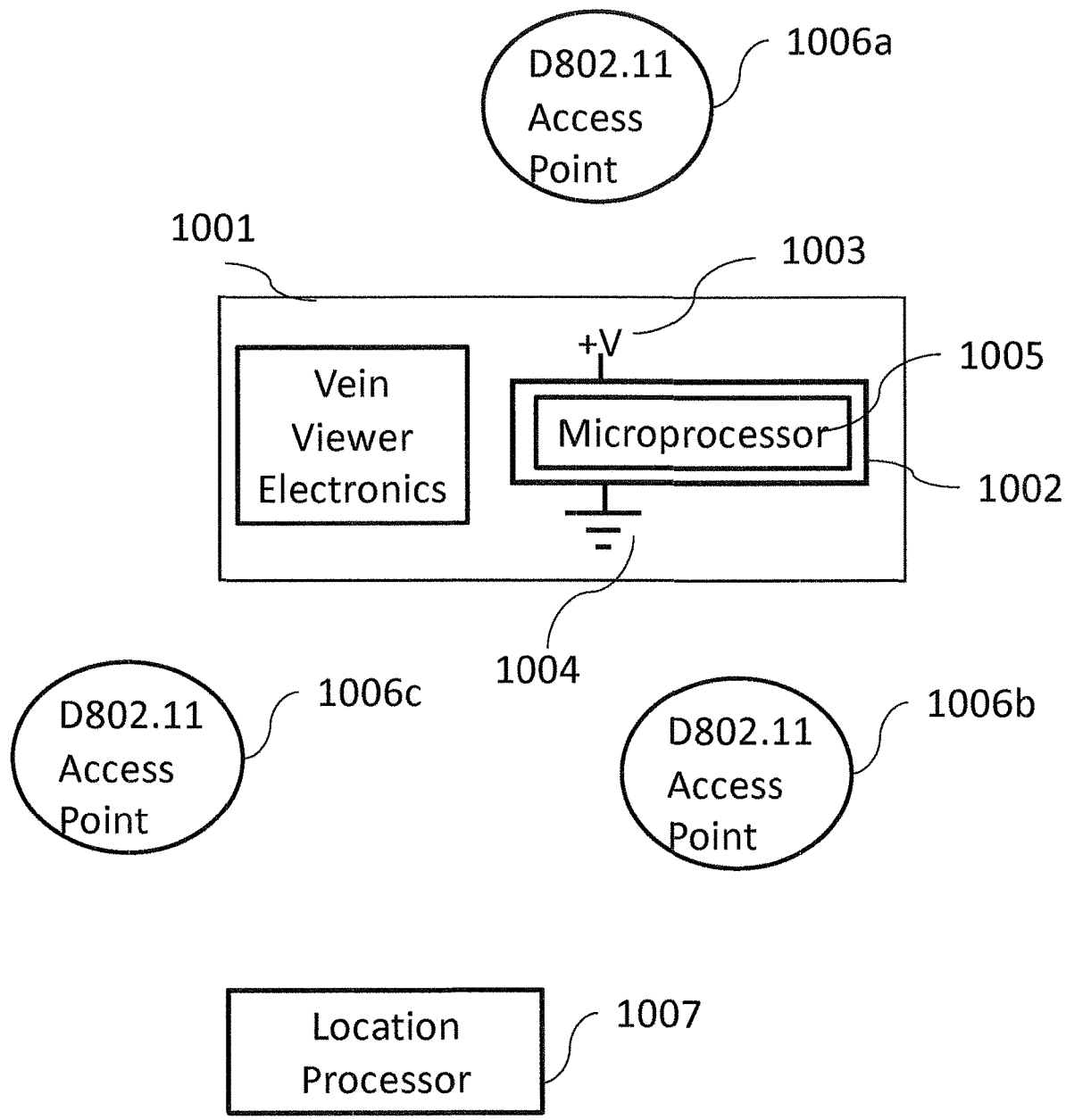
FIG. 10 illustrates a vein viewer with a radio for location within a radio network.

Previously in reference to FIG. 4, a radio module connected to or embedded in a computer system for controlling the vein viewing functions was described and integrated into a vein-viewing device, wherein the radio system communicated with the computer system. FIG. 10 illustrates a device 1001 having a radio module 1002 with a microprocessor 1005 for controlling the function of the radio 1002 connected to a voltage source 1003 and a ground 1004 of the device. However, in this embodiment, there is no data connectivity between the vein viewer electronics 1001 and the radio module 1002.

In this illustration, the radio module can include WLAN 802.11 radio communications. The microprocessor 1005 within the radio module 1002 can be programmed to periodically transmit beaconing signals that are received by 802.11 access points 1006a, 1006b and 1006c which are distributed throughout a location, such as a hospital. Location tracking algorithms are known in the industry, wherein, data based upon the received beacon signals are provided from the 802.11 access point 1006a-c, to a location processor 1007. The location processor 1007 then runs algorithms based upon the data received from the access points 1006a-c to determine the physical position of the device 1001 within the location.

The radios described in reference to FIGS. 1-4 can be utilized for both data communications as well as functioning as location beacons. For example, it is known that both Bluetooth radios and 802.11 WLAN radios can be utilized both for data communications and to function as a beacon for location systems.

Figure 11:
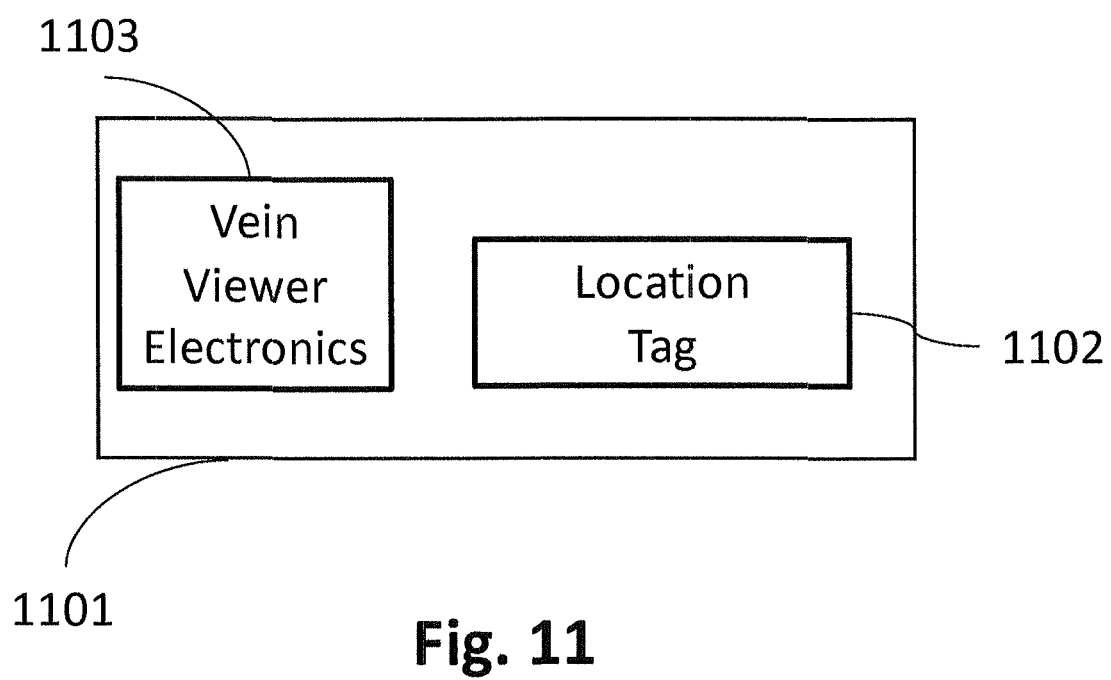
FIG. 11 illustrates a vein viewer with an embedded location tag.

An alternative method of detecting the position of a device is to incorporate a location tag or chip within the device. There are existing companies that have such tags, and infrastructure products for locating objects within an environment. One such example that can be found is the indoor real-time location system from Wavenet Solutions. FIG. 11 illustrates a vein visualization device having a Wavenet tracking device 1102 incorporated within the vein viewing device 1101. By utilizing the Wavenet infrastructure (not shown), the position of the device 1101 within a hospital or premise can be accurately determined. The invention herein is not limited to the location systems illustrated, and any type of location system can be incorporated in, or attached to, a vein viewing device.

The floor plan of a premise, such as a hospital, can be entered into a remote computer system that receives the real time location of all the devices within the premise. Rules can be established that change the operating behavior of each vein viewer depending upon its current location within the premise. The results of the rules can be communicated wirelessly to the vein viewing device. For example, it might be desirable to restrict the use of the device to a given location of a hospital. For example, the department purchasing a device might want to make certain that the device remains on a given floor or in a given department. Rules can be set up that in the event the location of the device is outside of the allowed operating area, a message is communicated by radio to the vein viewing device to shut down or to display warning information that it is out of the operating zone. This same shutdown operation can be performed when the device is detected leaving a premise, thereby acting as a theft deterrence.

Furthermore, geofencing can be used to enable or disable certain features. For example, if the device is in a pediatric ward, the mode of the device could be changed to features that are targeted at the pediatric population. When the device is moved to an adult unit, it could then convert to features that are targeted at adult populations.

Hospitals can be very large, and it is desirable to have various vein viewing devices geographically distributed about the hospital. This will ensure that a device is geographically closely available to a practitioner desirous of utilizing a vein viewer. Accordingly, the remote computer system can detect the location of each device within the hospital and can determine the optimal location for storing the device when not in use. Such information can be communicated by radio to the device and instructions displayed on the device as to where it should be stored.

The device can communicate usage information from the device to the computer system, such as, when and how often the devices are used. By tracking the locations of the vein viewing devices, and utilizing the information about how often the device is used at each location, appropriate load balancing analysis can be performed. For example, assuming it is determined that the devices are utilized three times more often in the emergency room, as compared with the intensive care unit, the remote computer system can allocate three times more units to the emergency room than the intensive care unit.

Tracking tags, or other tracking methods, can be attached to the rolling stands that hold the vein viewer device for hands free operation. Often the stands and the units get separated and the users waste a lot of time trying to locate them. When the remote computer system determines that a unit is physically separated from an associated rolling stand, it can communicate a message to the device, or the stand, or both, indicating where the associated partnering device is located.

Further, stands can be designed having various options and capabilities. The capabilities of the stands can be recorded in the computer system. When a user is seeking a stand with a particular capability, they can initiate a request from their vein viewing device which is communicated to the remote computer system, which in turn replies with the location of the desired stand. Illustrative features of stands are, stands with charging stations incorporated therein, stands with sterilization chambers attached thereto, etc.

The devices can be battery operated and need to be occasionally recharged. The location of the recharging stations can be detected by the computer system, and when a low battery condition is detected on a device, the location of a charging station can be communicated to the device and displayed to the user.

Medical equipment often needs to be periodically cleaned to prevent transmission of infections. The frequency of the cleaning is often a function of the location or movement of the device within a hospital. For example, as the device is moved from an area of the hospital housing infectious patients, to a less stringent area, extensive cleaning might be prescribed by the hospital's protocols. The remote computer system can detect such movement of the vein viewing device and can send a message to the device instructing the user to disinfect the system. If the user fails to confirm that they have disinfected the unit, the units can shut down, and the remote computer system can send appropriate warnings to the supervisors.

Further, the cleaning locations for the device are often at predetermined locations. The remote computer system can be arranged to detect whether the device is taken to the predetermined location when cleaning is required. If the user fails to take the unit to the prescribed cleaning location, an appropriate warning can be initiated. In response to this warning, the device can prevent itself from performing the vein viewing operation and can provide appropriate warning information to the user and/or appropriate supervisors.

It is desirable to know when and where within a hospital a vein viewing device is utilized. Accordingly, the device can communicate to the remote computer system each time the device is utilized. This information can be combined with the location of the device at the time of utilization, to determine in which patient's room the device was utilized. This information can be used to drive billing information.

It is possible to provide the vein viewing devices to the hospitals on a subscription model. In this case the device is provided to the hospital for free, or on a discounted basis, and the hospital is billed based upon utilization. In this case, it would be very helpful to have records of when and where the devices were utilized. According, by transmitting the utilization information from the device to the remote computer system and combining this information with the real time location of the devices, a log of when and where the devices were utilized can be developed. The subscription model now can be quite sophisticated, and billing adjusted based upon where, when and how often the devices are utilized.

When it is determined that an IV line should be inserted into a patient, or that blood should be drawn from a patient, or that a drug should be administered to a patient, such and order is initiated by a doctor or nurse, and often entered into an automation system. The automation system communicates to the nurse, via printed instructions or electronically, the desired action to be taken for a given patient. However, there often is no methodology to ensure that the instructions were appropriately followed. The usage of the vein viewing device can be communicated by radio to the computer system that detects and stores the real time location of the devices. Such computer system can compare the orders from the automation system with the utilization and location of the device. If the device is used at the wrong time, or the wrong locations, or is not used at all, appropriate warnings can be generated by the system. Further, the vein viewing devices can record and store the vein patterns of the patient. Such vein patterns are unique biometric measures for each patient. The vein device can transmit by radio the vein pattern of the particular patient to the computer system as confirmation that the procedure was performed on the appropriate patient.

It is possible to have the user of the vein view device identified and communicated to the computer system. For example, the user may be required to enter a unique key sequence into the device, or into a third-party device (such as a smartphone) in radio communications with the device, before the device is enabled. Alternative, the device, or the third-party device can detect unique biometrics of the user, such as but not limited to, vein patterns, fingerprint patterns, iris patterns, facial recognition, walking gate information, voice recognition, to name a few.

Accordingly, by transmitting to the computer system which handles the real time location of the device, the user information and the utilization information for the device, the computer system has a very complete picture of who (user), when and where the device was used. This is particularly useful information when trying to determine what might have been the cause of an infection. Often when an infection is detected, it is desirous to "lookback" over time to determined who performed the procedure that caused the infection. Based upon the type of infection, it often can be estimated when the offending procedure was performed. For example, assume a patient gets an infection, and it is determined that the offending procedure most likely occurred four days prior, the records of the computer system can be checked to determine which user performed the offending procedure. Appropriate remediation actions can then be taken.

It is often very important for a hospital to determine the usage patterns for medical equipment. By combining the user information, the utilization information and the location information, all available at the computer system, reports can be generated showing the utilization patterns of the device. For example, a report can be generating showing which shifts utilize the devices the most. Other examples of relevant information are: the time the devices are used within a shift, departmental usage, day of week usage trends, how long the devices are utilized for each procedure. This information can be very useful for training purposes, for determining additional purchase requirements, and for geographic distribution of units for load balancing.

In the event the device is in radio communication with a third-party device (such as a smart phone), the display screen on the smartphone can be utilized for displaying in graphical form the utilization data.

Hospitals and other locations where medical equipment is used often have protocols in place for cleaning and sterilizing the equipment. In some cases, a schedule might be put in place to clean the equipment. For example, the schedule could dictate that the equipment be cleaned once a day, or at the start of each shift, or as often is the case, before or after each use. Further, the cleaning protocols might vary for different departments, or even different areas within a department. For example, a protocol is sometimes established that the medical equipment should be periodically cleaned, however it must be cleaned each time the units is removed from a hospital room housing an infectious patient.

The cleaning methodologies vary by hospitals, but often involves a spray and wipe technique consisting of applying a cleaning liquid to the equipment, allowing the liquid to remain on the equipment for 3 to 5 minutes, and then wiping the liquid off the equipment. This approach is not always effective given that the liquid might not be applied to all surfaces of the equipment, and therefore, the cleaning will only be partially completed. A further practical challenge is that this is a long procedure, and given the nurses busy schedules, they often do not have the time to properly clean the equipment, and often skip this cleaning step. Ignoring or bypassing the hospital's cleaning protocol can lead to increased infections within the hospital.

There are various types of cleaning equipment for cleaning and/or sterilizing medical equipment. For example, UVC light disinfection chambers, such as the Flashbox and Flashbox by Clordisys Applications|Healthcare (clordisys.com) allow a nurse to place medical equipment within the chamber. The literature indicates that "The FLASHBOX-mini contains 1 shelf to support the item(s) being disinfected. It simply plugs into any wall outlet. The disinfection chamber produces an efficient UVC output of 2000 µW/cm2 to get a greater than 99.99% reduction of MRSA and a 99.99% reduction of spores like and *C. difficile*." The chamber has a door which can be opened to insert and remove the medical equipment. Upon shutting the door to the chamber, a UVC light is generated and baths the equipment in the light. It is known that UVC light kills bacteria and viruses. The intensity of the UVC light, and the duration of the light bath, can vary by application, and generally the more critical the cleaning requirement, the brighter the light and/or the longer duration of light bath.

There exist other types of cleaning chamber that employ other cleaning and sterilizing methodologies. For example, the Minidox-M by Clordisys Products|Minidox-M (clordisys.com) is a chlorine dioxide gas generation system which utilizes chlorine dioxide gas to bath the medical equipment placed within the chamber. There are many other types of gases utilized in chambers for cleaning and sterilizing equipment. Still further, some chamber utilize heat to clean and or sterilizing the equipment. Still further, some equipment utilizes radiation energy.

While the cleaning chambers described could appropriately clean and/or sterilize a vein viewing device, the geographical location of the chamber, such as at the nursing station, makes it difficult for a nurse to frequently utilize them.

Figure 12:
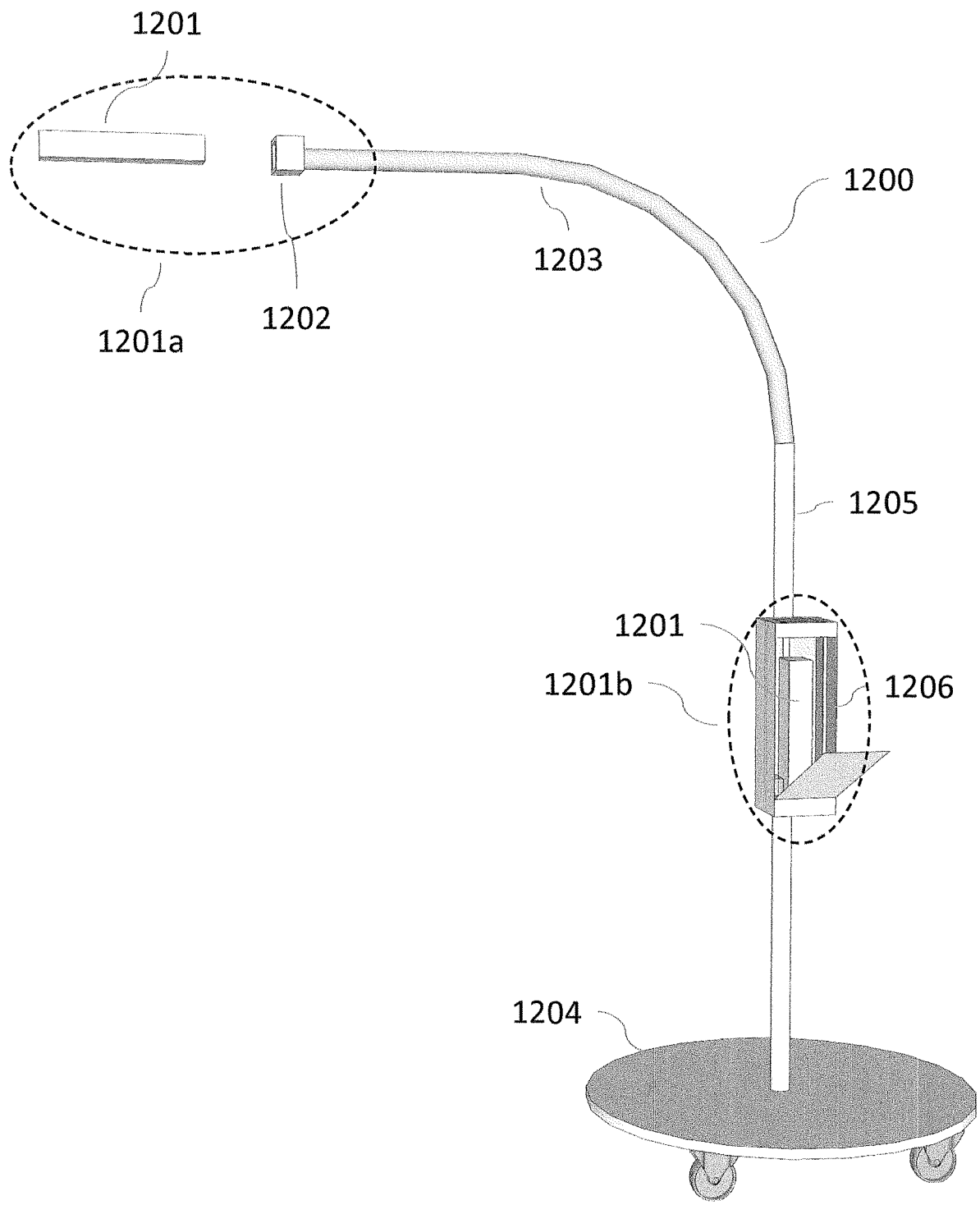
FIG. 12 illustrates a rolling stand for securing a vein viewer and comprising a UVC chamber for storing and cleaning the vein viewer.

An embodiment of the present invention is shown in FIG. 12 wherein a rolling stand 1200 includes a wheeled base 1204 that allows the entire stand 1200 to be transported about the premise. A rigid vertical pole 1205 connects the wheeled base 1204 to a flexible adjustable arm 1203. The rigid vertical pole 1205 supports the flexible adjustable arm 1203 which in turn supports a cup 1202 which is configured to receive and hold in place a vein viewer 1201. Position 1201*a* shows the vein viewer 1201 positioned to be received by the cup 1202. When a practitioner wants to utilize the device 1201 in a handheld mode, the device is removed from the cup 1202 and is supported by the practitioner during procedures. When the practitioner wants the device 1201 held in a fixed position, so both hands are available to perform a procedure, the device 1201 can be placed in position 1201*a* and secured within the cup 1202. When the vein viewer 1201 is position within the cup 1202, the flexible adjustable arm 1203 can be manipulated to appropriately position the vein viewer 1201 in relationship to a patient to optimize the vein viewing procedure. For example, the flexible adjustable arm 1203 can be manipulated by the user so that the device 1201 is eight inches perpendicularly away from the location to be imaged, with the bottom surface of the device 1201 parallel to the location to be imaged.

FIG. 12 further shows a cleaning chamber 1206 rigidly attached to the rigid vertical pole 1205 of the rolling stand 1200. An electrical power cord (not shown) connects the cleaning chamber 1206 to a power source. After a procedure, a user can place the vein viewer 1201 can be placed at position 1201*b* into the cleaning chamber 1206.

Figure 13A:
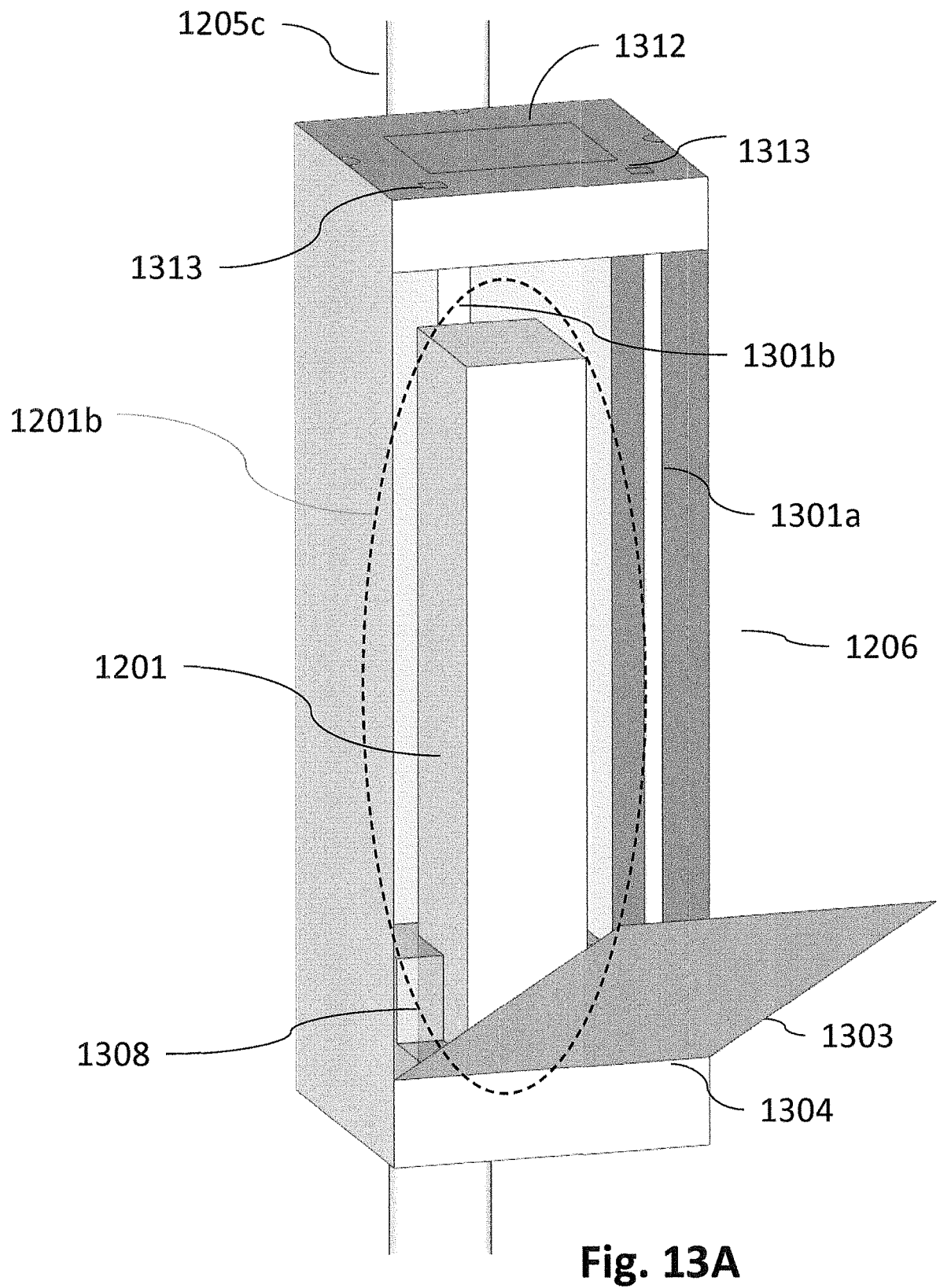
FIG. 13A is a solid view showing in greater detail the UVC chamber of FIG. 12.
Figure 13B:
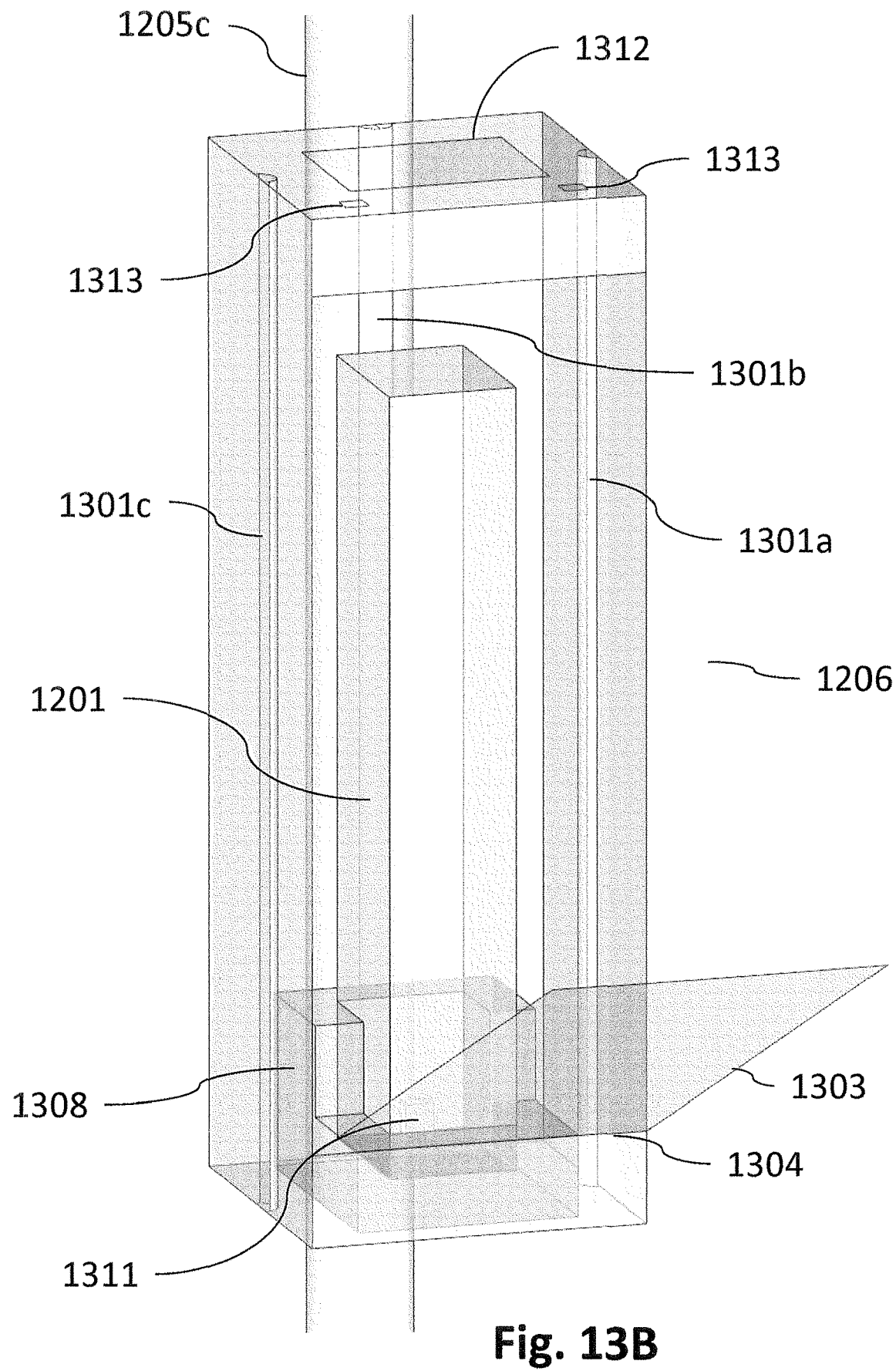
FIG. 13B is a ray trace of the UVC chamber of FIG. 13A.

FIGS. 13A and 13B illustrate the cleaning chamber 1206 of FIG. 12 in greater detail. FIG. 13A is a solid rendering and FIG. 13B is a transparent ray trace rendering of FIG. 13A. Referring to both FIGS. 13A and 13B, the cleaning chamber 1206 generates UVC light by electrically energizing a plurality of UVC light sources 1301*a*, 1301*b* and 1301*c* which are positioned within the interior of the cleaning chamber 1206. Further the inside of the chamber can be mirrored, or have other reflective coatings, to ensure that the UVC light properly baths the exterior surfaces of the device 1201 when it is place within the chamber 1206 at position 1201*b*. A front door 1303 is connected via a mechanical hinge 1304 to the chamber 1206, wherein the front door can be opened to allow a user to insert and remove the vein viewer 1201. The front door 1303 can also be closed so that the vein viewer 1201 is completely enclosed within the cleaning chamber 1206. Gaskets or other sealing can be provided between the front door 1303 and the cleaning chamber 1206 so that when the door is a closed position none of the UVC light leaks out of the cleaning chamber 1206. Still further, the front door 1303 can incorporate a window that does not allow UVC light to pass (not shown), which allows a user to view to view the device 1201 during the cleaning cycle. Further, the interior of the cleaning chamber has a transparent cradle 1308 which is mechanically configured to receive and hold in place the vein viewing device 1201 when it is placed within the chamber 1206. A sensor can be incorporated (not shown) which detects when the front door 1303 is in the closed position. Further, a locking mechanism, such as a solenoid can be utilized to lock the front door to prevent opening while the UVC light is bathing the device. A display 1312 and input keys 1313*a* are position on the top of the device. The display 1312 could be a touch screen.

To enable complete cleaning, the UVC light must bathe all of the surfaces of the device 1201. To enable this, the physical support structure 1308, which physically contacts the device 1201, can be made from a translucent material, or any material which allows UVC light to pass therethrough. A male electrical charging connector 1311, such as a UBC C connector, can be positioned at the bottom of the cleaning chamber 1206. The connector 1311 can be positioned so that it mates with a female connector (not shown) positioned on the bottom surface of the device 1201. Accordingly, through this connection scheme, it can be determined when the device is properly inserted into the cleaning chamber 1206, and charging energy can be applied to the device 1201 to recharge it's batteries.

Figure 14:
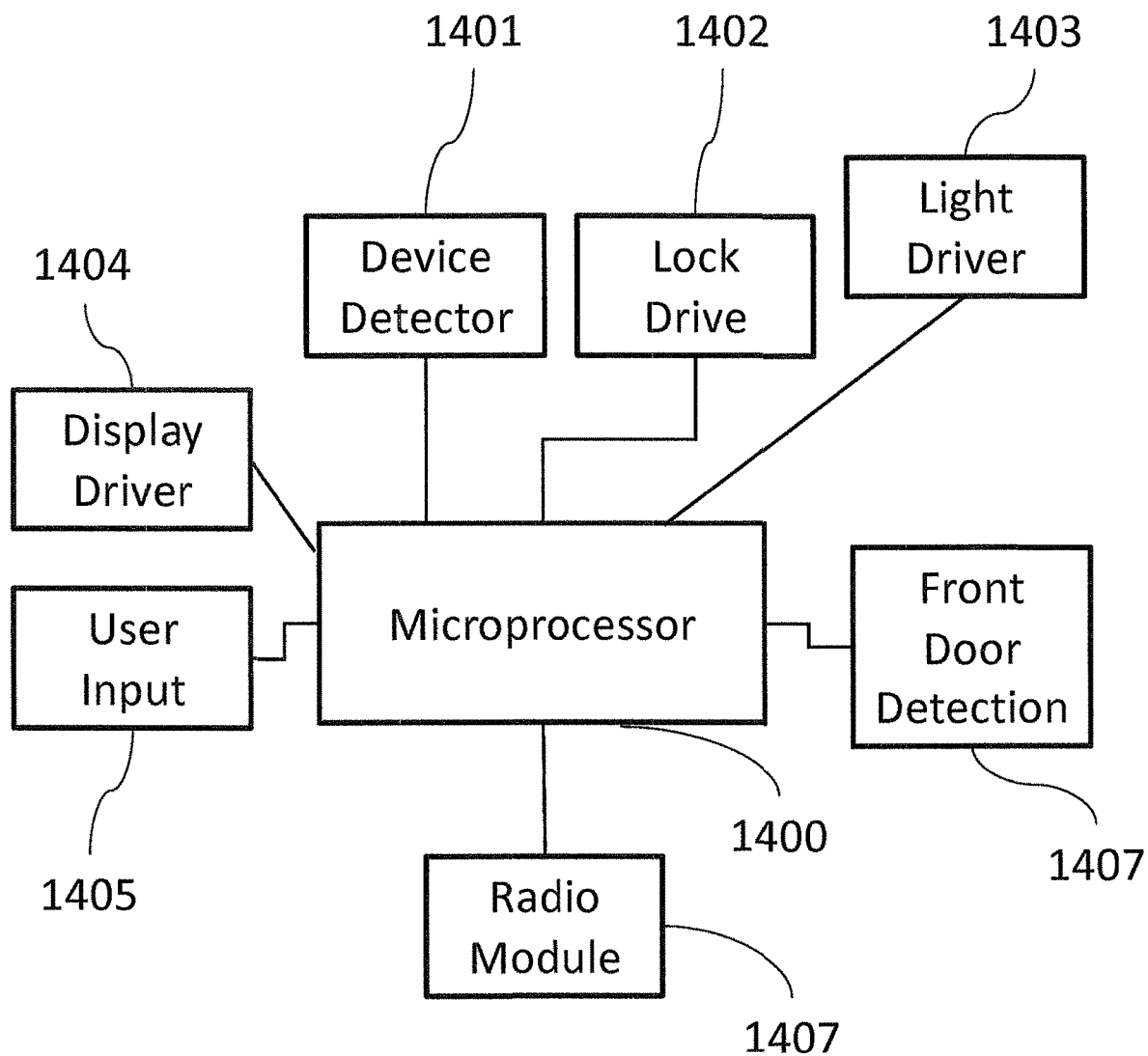
FIG. 14 illustrates a block diagram of the UVC chamber.

FIG. 14 is an electrical block diagram of the electronics within the chamber 1206 of the embodiment described with reference for FIGS. 12A, 13A and 13B. A microprocessor 1400 provides the control logic for the chamber 1206. A device detector 1401 provides indication to the microprocessor 1400 when the device 1201 is properly situated in the chamber 1206. This device detection can be via the mating connectors 1311 and 1312, or can be a physical mechanical switch, or any other method of detecting the proper positioning of the device 1201. A locking mechanism, such as a solenoid, is driven by a lock drive 1402 which is controlled by the microprocessor 1400. A light driver 1403, for electrically driving the light sources 1301*a-c*, is enabled by the microprocessor 1400. A front door position detection mechanism 1407 provides a signal to the microprocessor 1400 indicating the open or closed state of the front door 1303. A display driver 1404 is responsive to command signals for the microprocessor 1400 to drive a user display, such as, for example, an LCD display or display LEDs. An input circuit 1405 receives user inputs, such as for example, keypad depressions, or a touch screen, and communicates such information to the microprocessor 1400. The microprocessor 1400 can connect to a radio module 1406 to enable communications with the devices 1201, as well as any other network connected remote computer systems.

FIG. 15 is an illustrative workflow of the present invention. In block 1401 the rolling stand 1200 and vein viewer 1201 are positioned with the hallway of a hospital. The vein viewer 1201 is positioned within and mechanically held in the chamber 1206 by physical support structure 1308. The chamber 1206 is connected to a power source. The vein viewer 1201 is electrically connected via connector 1311 and receives charging energy from the chamber 1206 for charging internal batteries. At this point in time the front door 1303 is shut. If the vein viewer 1201 has not been cleaned, the front door 1303 is locked and a cleaning cycle is run. Upon completion of a cleaning cycle, the front door 1303 is unlocked. Block 1402 illustrates an example of how a user utilizes the vein viewer 1201. The chamber 1206 is unplugged from the power source. The user rolls the stand 1200 into a patient's room and removes the vein viewer 1201 from the chamber 1206. The vein viewer 1201 can then be used in a handheld mode to locate a patient's veins. Once an appropriate vein location is identified, the vein viewer 1201 is inserted and mechanically connected to the cup 1202 and the user can manipulate the flexible arm 1203 to position the vein viewer 1201 to an appropriate position. The procedure is then performed and thereafter, the vein viewer 1201 is placed back into physical support structure 1308 within the chamber 1206. The user then shuts the front door 1303 which is automatically locked. In block 1403 the stand 1200 is then rolled back to the hallway and the chamber 1206 is plugged into the power source. The cleaning cycle runs and upon completion the front door is unlocked. The vein viewer is charging while it is housed in the chamber. Alternatively, the rolling stand or the chamber 1206 can have a rechargeable battery capable of driving the chamber without requiring the unit be plugged into the wall.

In the above embodiment described with reference to FIG. 15, the front door 1303 automatically unlocked after the cleaning cycle. As an alternative embodiment, to prevent theft or non-authorized used of the vein viewer the door can remain locked unit and unlocked under certain circumstances as previous described.

The vein viewer illustrated in FIGS. 1-4 can connect via the incorporated radio to remote computer systems having much larger processing capabilities than that contained in the vein viewer. The bandwidth of radio networks are capable of communicating images at video rates. As an embodiment of the present invention, the vein viewer captures images of a patient's vasculature at video rates, and communicates such video image over the radio network to a more powerful remote computer system. The more powerful remote computer system can be, for example, a personal smartphone, local computers within a facility, or can be cloud base computers remotely located.

The prior art vein viewers run vein detection algorithms internally that processes the captured images of the vasculature to eliminate false signals and eliminate noise. It then outputs a processed image of the veins to the projector which in turn projects a visible image onto the patient. Such algorithms can be substantially improved using machine learning and AI techniques to determine an enhanced algorithm. However, a single vein viewer does not capture a broad enough sample of images of the vasculature, and further, does not have enough memory to store the millions or billions of image desirable for machine learning. As an embodiment of this invention, each vein viewer is configured to stream via the radio the real time images of the vasculature to a remote computer system which stores the images in a database. In this manner the database very quick obtains a very large database of vein images. This large set of images are then utilized to train machine language algorithms to differentiate between the noise in the images and the actual vein pattern. The developed algorithm can then be communicated via the radio network to the vein viewers, wherein the internal vein detection algorithm is replaced and/or augmented by the resulting algorithm. As yet a further embodiment, the resulting algorithm can be manually entered (without radio communications) into the vein viewers during the manufacturing stage, or alternatively during the servicing of a vein viewing device.

Vein viewers are capable of displaying valves within the vasculature. The process involves the user applying pressure at a preselected position of a vein and wiping blood from the vein from the pressure point towards the heart. While the pressure remains, the blood in the vein is viewed backfilling to the location of a valve, and only after the pressure is released does the blood fully flow in the vein. While this technique works, it if very difficult teaching the nursing community how to implement this technique. It would be desirable to utilize image processing algorithms to detect the position of the valves. However, the computer and memory capacities of a vein viewing device are insufficient to implement such algorithms. As an embodiment of the present invention, the video image of the vein image captured by the vein viewer is communicated by the radio to a more powerful remote computer system, such as a smartphone, local computer, or cloud computer. An algorithm is run in the remote computer system to detect the valve position. When the valve position is identified, the remote computer system communicates the valve position via the radio network to the vein viewer. The vein viewer responds to the valve position information received by projecting a unique identifier onto the patient. The identifier can be, for example, a unique color, an arrow pointing to the valve, a box surrounding the valve. As a further embodiment, the algorithm at the powerful computer can also determine the rate at which the vein refills during the wiping procedure. This speed information can be communicated via the radio back to the vein viewer which in turn projects the speed information.

As an alternative embodiment, the processing capability of the vein viewer can be increased, and the valve detection algorithms run locally by the vein viewer.

An IV needle dwelling in a patient occasionally results in infiltration at the insertion site. When this occurs blood pools internally resulting in painful bruising and many other potential detrimental events. The image captured by the prior art vein viewers contain some data indicative of such infiltration, however, it is difficult to extract such infiltration data and project a representation of the infiltration. As an embodiment herein, the video image of the vein image captured by the vein viewer is communicated by the radio to a more powerful remote computer system, such as for example, a smartphone, local computer, or cloud computer. An algorithm is run in the powerful remote computer system to detect infiltration. Infiltration can be extracted by algorithms look for pooling of blood that is other than vein shaped. When the infiltration is identified, the powerful remote computer system communicates the infiltration position via the radio to the vein viewer. The vein viewer responds to the infiltration position information received by projecting a unique identifier onto the patient. The identifier for the infiltration can be, for example, a unique color, an arrow pointing to the valve, a box surrounding area of interest.

As an alternative embodiment, the processing capability of the vein viewer can be increased, and the valve detection algorithms run locally within the vein viewer.

The image captured by the prior art vein viewers contain some data indicative of the pulse rate of the patient, however, it is difficult to extract such pulse data and project a representation of the pulse. As an embodiment herein, the video image of the vein image captured by the vein viewer is communicated by the radio to a more powerful remote computer system, such as, for example, a smartphone, local computer, or cloud computer. An algorithm is run in the powerful remote computer system to determine the pulse. The pulse can be extracted by algorithms look for optical artifacts in the veins caused by the heart beating. When the pulse is determined, the powerful remote computer system communicates the pulse rate via the radio to the vein viewer. The vein viewer responds to the pulse rate information received by projecting the pulse rate onto the patient. The representation of the pulse rate can be, for example, the projection of a pulse rate number, or projection of a graph or chart showing the pulse rate as a function of time. Furthermore, the pulse rate can be sent to the medical record keeping system as an option.

As an alternative embodiment, the processing capability of the vein viewer can be increased, and the pulse detection algorithms run locally within the vein viewer.

As a further embodiment, image processing algorithms can be utilized on the powerful remote computer system to categorize the veins, and segments of the veins, within the images based upon several parameters, such as, for example, vein width, vein depth, blood flow rate, vein location on the patient, location of valves, and previous puncture marks. The algorithm can set various weightings to each individual parameter and determine an overall grade of each vein segment. As an embodiment, the highest overall grades can correlate to vein segments that are most suitable for a procedure, such as, for example, insertion of an IV or a blood draw. The results of the overall grade are then communicated by the powerful remote computer system to the vein veiner wherein a visual indication of the grade is displayed on the vein viewer and/or projected onto the patient. The projection or the overall grade can be, for example, numbers, or colors. For example, the vein pattern can be projected onto the patient wherein the higher overall grades (and therefore the best vein segments to access) are shown in green, the middle overall grades are in yellow, and the low overall grades are in red.

As an alternative embodiment, the processing capability of the vein viewer can be increased, and the vein selection algorithms run locally within the vein viewer.

The existing vein viewers capture the vascular image with a relatively small field of view. For example, assuming the vein viewer has a field of view of 3" by 3", to view the entire vasculature of a patient's forearm, the user of the vein viewer has to move the device along the length of the forearm to sequentially view the forearm. In this manner, the vasculature of the entire forearm can be time sequentially viewed, but at any given time only the 3" by 3" field of view is visible. As previously described herein, the video image (or sequential pictures) captured by the vein viewer can be communicated via the radio to a more powerful remote computer system, which in turn can run stitching algorithms to stitch together the individual pictures within the video image into a larger image. For example, in the case of a patient's forearm, a single image of the vasculature of the entire forearm is stitched together. The stitched image of the forearm can then be stored in the powerful remote computer system or communicated via the radio network to be saved a medical database. Still further, the stitched image can be communicated to the vein viewer. The vein viewer can comprise a high-resolution display screen that then displays the stitched image. Still further, the stitched image can be communicated to a companion device, such as, for example, a smart phone or an IPAD, wherein the stitched image is displayed. Still further, the stitched image can be processed using vein finding algorithms such that a full vein pattern can be created and that vein pattern can be annotated for the user to aid them in making vein selections.

Figure 16:
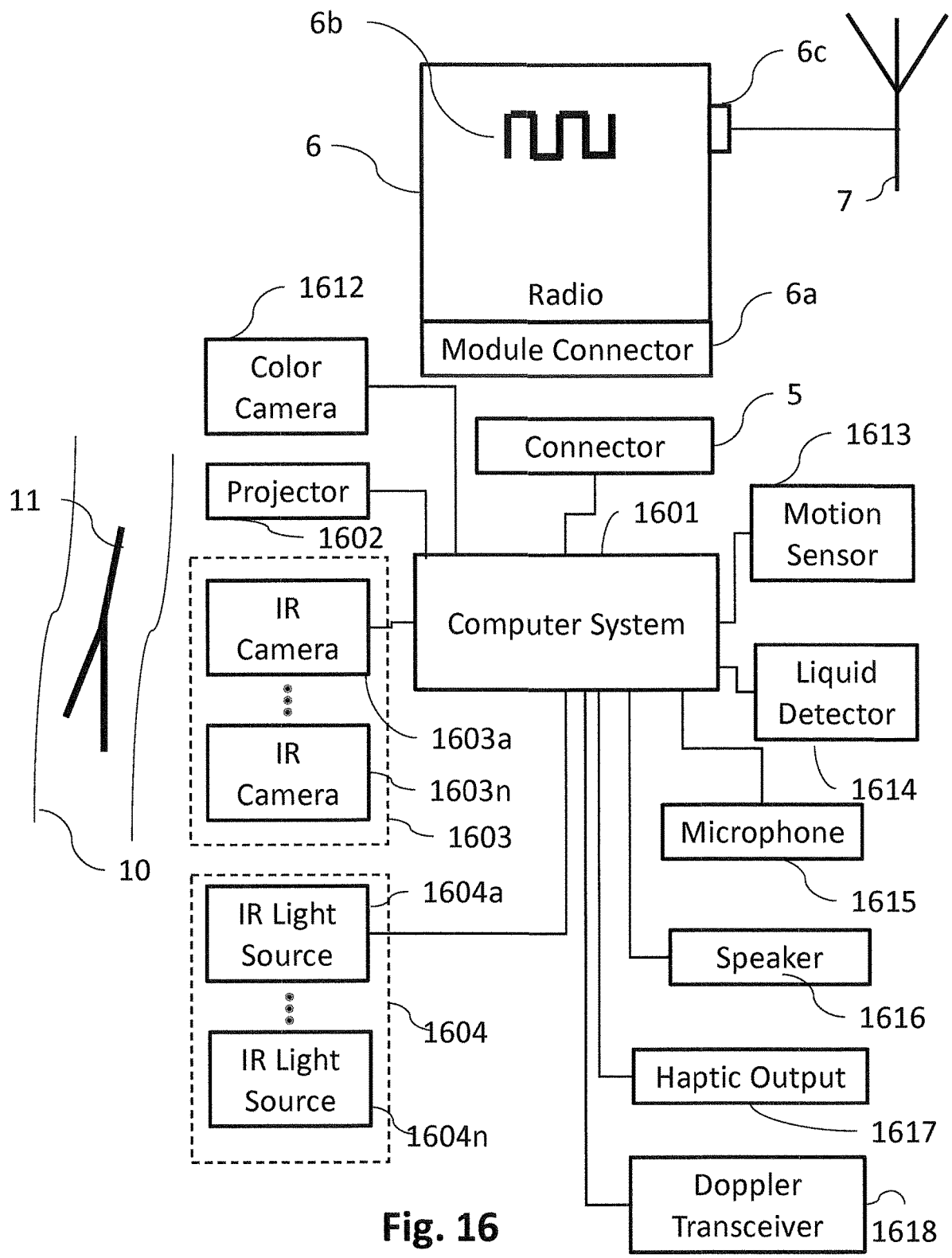
FIG. 16 illustrates a vein viewing device with capabilities to detect cleaning.

FIG. 16 illustrates an embodiment wherein a color camera 1612 and multiples IR cameras 1603 and multiple IR lights 1604 are incorporated into the vein viewer. One or more IR light sources 1604 (1604a-1604n), each projecting a different frequency of light, directs IR light at a patient 10, wherein the veins 11 of the patient absorb the IR light thereby reflecting an IR light pattern representative of the veins 11 towards one or more IR cameras 1603 (1603a-1603n). Each IR camera 1603 is configured to capture only the specific frequency of IR transmitted by the corresponding IR light source 1604. Each IR camera 1603 communicates the captured image to a computing system 1601, which in turn processes the image to accentuate the vasculature and communicates the processed image to a projector 1602 which projects in visible light, the image onto the patient 10. The cameras 1603 and the projector 1602 are optically aligned so that they image and project at the same locations on the patient 10. In the present embodiment, the computing system 1601 connects to an electrical and mechanical connector 5 which in turn connects to a mating radio module connector 6a of radio module 6. The radio module can include antenna 6b printed on the module, and or, can have a remote antenna connector 6c for connecting to a remote antenna 7. A color camera 1612, such as, for example, a CCD or CMOS camera, is optically aligned with the field of view of the projector 1602 and captures a color visible image (can be video or still images) of the patient 10. This captured visible image of the IR is communicated to the computing system 1601. In the present embodiment, the computing system 1601 connects to an electrical and mechanical connector 5 which in turn connects to a mating radio module connector 6a of radio module 6. The radio module can include antenna 6b printed on the module, and or, can have a remote antenna connector 6c for connecting to a remote antenna 7. The images captured by the color camera 1612 and the IR cameras 1603 can be communicated by the radio module 6 to remote computers systems.

Still further the vein viewer can incorporate a doppler transducer 1618 which is capable of detecting the flow or the blood within the patient's veins. The doppler transducer communicates with the computing system 1601.

As an embodiment of the present invention, the vein viewing device of FIG. 16, communicates via the radio module 6 the multispectral images captured by the IR cameras 1603 and the color camera 1612 to a remote computer system (not shown), such as, for example, smart phones, PDAs, tablet computer, local computers, remotely located computer, or cloud computer. It is known that the blood oxygenation of a patient can be determined from multispectral images of a patient. The remote computer system processes the multispectral images received from the vein viewer, and determines the blood oxygenation at various locations within the image. The various locations can be, for example, a grid pattern. The blood oxygenation levels can then be communicated to the vein viewer, or any other device on the radio network. The vein viewer, or other network devices, can display the blood oxygenation levels as a colored heat map superimposed over the vein pattern of the patient. For example, the color scale Red, Orange, Yellow, Green, Blue Indigo, and Violet can be utilized wherein the highest level of oxygenation is indicated in red, the lowest levels in violet, and all intermediate levels spread between red and violet. Further, the projector 1602 of the vein viewer can project the heatmap onto the patient's body so that the oxygenation levels can be determined while looking at the patient. While the representation of the blood oxygenation has been described as a heatmap, there are many other ways the blood oxygenation can be represented, such as, for example, displaying percentages directly in the image. Further, contour lines can be shown around the displayed percentages indicating the region relating to the display percentage.

The color camera 1612 of FIG. 16 is utilized to capture an image, or sequence of images such as a video, of the patient 10. The color camera 1612 is optically arranged to have the same field of view of the IR cameras 1603. Accordingly, in operation the color camera 1612 captures what is happening above the surface of the patient 10, and the IR camera 1603 is capturing the vein pattern 11 below the surface of the patient 10. The computer system 1601 can merge the output of the color camera 1612, and the output of the IR cameras 1603 into a single image and communicate the image via the radio module 6 to remote computer system (not shown) where the images are archived as medical records. Alternatively, each of the video streams from the color camera 1612 and the IR cameras 1603 can be transmitted independently via the radio module 6 to the remote computer system where they are stored as medical records.

It is known that certain veins within a patient are safer to access than other veins. For example, the basilic vein is often referred to the vein of last resort for venous access given its position relative to nerves in the arm. Utilizing the video stream from the color camera 1612 and the IR camera 1603 the position of the veins 11 relative to the patient's 10 anatomy can be determined by the computer system, 1601, or a remote computer system (not shown), and based upon such information, the names of the imaged veins can be identified. The identified names of the vein can be projected by the projector 1602 onto the patient 10, wherein the name is superimposed over the related vein. Further, a database of the preferred veins can be stored and the most preferred veins can be displayed as unique colors, or other identification indications.

Since vein access is a frequent procedure, communicating the color and IR signal to the remote computer system will result in a very large video database of captured procedures. The remote computer can then utilize artificial intelligence to evaluate the video streams to determine a host of parameters, such as, for example, how often an attempted procedure is successful, the duration of each procedure, whether proper cleaning techniques were utilized, whether the person inserting the needle wiggled the needle under the surface (a disallowed technique commonly referred to as "digging"), and whether the best or correct vein was accessed. It is also possible to associate the user of a vein viewer and communicate the user info to the remote computer system, and to communicate the date and time the image was captured. Reports can be generated based upon the user, and/or date and/or time tracking and the host of parameters resulting from the artificial intelligence processing. Spreadsheets and graphs can be generated based upon such reports. Threshold limits and/or ranges can be established, wherein if, one or more of the host of parameters is out of range, alarms are created and sent to identified systems. For example, is a nurse is "digging", and immediate warning signal can be sent to a supervisor via the radio network.

Cleaning of medical equipment is critical to prevent infections from spreading within a hospital. Many hospitals have protocols that require wiping down the vein viewer with a cleaning agent after use. Unfortunately, this cleaning policy is often ignored and there is no practical way to monitor compliance. In one embodiment of the invention, after each use of the device, the vein viewer provides a message to the user requesting that the user confirm that they have cleaned the vein viewer. The message can be delivered via, for example, the display on the vein viewer (not shown), an audible message on the vein viewer, or a message to a companion device, such as a smart phone. The user must then within a predetermined period enter a confirmation that they have completed the cleaning process. The confirmation can be entered by various input methodology, such as, through a keypad, fingerprint, vein biometrics, voice confirmation, or confirmation on the companion device. If the user fails to enter confirmation of the cleaning, the vein device communicates such failure by radio to a supervisor, or recorded in a remote computer.

The above method of having a user confirm cleaning relies on the honesty of the user. It is possible that they confirm cleaning even if they did not clean the device. Referring to FIG. 16, as a further embodiment, the color camera 1612 can continue to capture a visible color video stream after the vein unit is utilized. The video stream can be analyzed by the computer system 1601, or a remote computer system receiving the video stream via the radio module 6, to determine visually whether the cleaning has occurred. There are many visual cues associated with cleaning, such as, for example, detection of a cleaning wipe passing in front of the camera, or detection of movement of the vein viewer normally associated with cleaning.

The vein viewer of FIG. 16 can also incorporate a motion sensor 1613, such as an inertial sensor or a gyroscope, which is utilized by the computer system 1601 to detect motion of the vein viewer associated with a cleaning process. Still further, the vein viewer can also incorporate a liquid detector 1614 with its sensors on the outer portion of the vein viewer, which generates a signal for the computer system 1601 upon detection of a liquid, such as a cleaning agent, being applied to the vein view. Still further, the vein viewer can incorporate a microphone 1615, wherein a unique noise pattern associated with the cleaning of the vein viewer is communicated to the computer system 1601 which in turn algorithmically detects the cleaning. Accordingly, the confirmation of cleaning can be determined from one or more: the user entry as described previously, information detected by the color camera 1612, information derived from the motion sensor 1613 and information derived from the liquid detector 1614 or information from the microphone 1615. As a further embodiment, the data from the motion sensor 1613 or the liquid detector 1614 can be communicated to a remote computer system where is processed, and the results communicated back to the vein viewer, other remote computer systems, or store in medical records.

Another method of verification is the statistical evaluation of the length of time for the procedure. For example, some wipe instructions require 3 minutes of cleaning. By calculating the time between the end of the venipuncture procedure and the completion of the cleaning procedure and applying a statistical analysis you could determine that the average nurse is taking 7 minutes for that period, but one nurse is taking 4 minutes. This may indicate that that nurse isn't following the 3 minute rule.

Before performing venipuncture, hospital protocols require that the location of the puncture site be sterilized with, for example, a sterile alcohol prep pad (70% isopropyl alcohol) or Chlorhexidine gluconate scrub or povidone-iodine. The present invention provides an approach to utilize the vein viewer of FIG. 16 to confirm that the puncture site was appropriately cleaned prior to the venipuncture procedure. As an embodiment, the vein viewer is positioned (can use the stand of FIG. 5b) so that the field of view of the color camera 1612 falls upon the location on the patient 10 where the venipuncture is going to be performed. A color video image is transferred from the color camera 1612 to the computer system 1601, and optionally to remote computers systems via the radio module 6. The computer system 1601, or the remote computer system, processes the video images to confirm that the sterilization has occurred. The computer system 1601, or remote computer, can utilize artificial intelligence routines that are trained to detect the sterilization activity. Specific movements within the video stream corrolate with the act of sterilizing a patient. For example, grabbing the agent, opening the sterile packaging, wiping motion upon the patient. Alternatively, the video images can be made available for viewing by a human operator, who views the videos to confirm the sterilization has occurred. If it is determined that the sterilization protocol has not been followed, a message is communicated to an appropriate location, such as a supervisor, or stored in a medical database for latter review.

Figure 17:
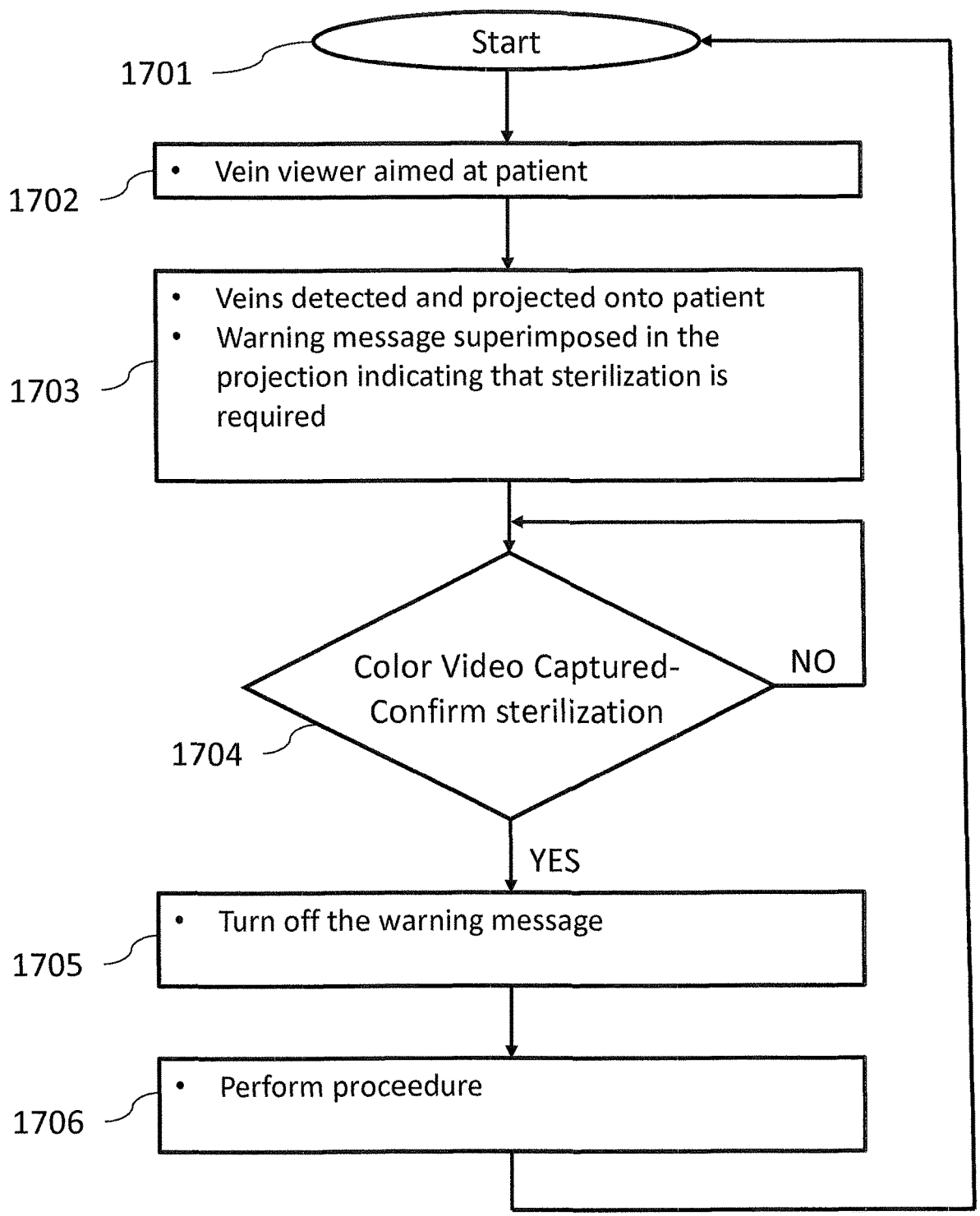
FIG. 17 is a flowchart showing the operation of a vein viewing device that detects cleaning.

FIG. 17 illustrates a further embodiment of the present invention. Step 1701—The vein viewer is positioned (can be in the stand of FIG. 5b) to detect the veins 11 of the patient. Step 1702—The vein pattern 11 is detected by the IR camera 1603 and a visible image of the detected veins is projected by the projector 1602. A warning message, such as large red letters, is included in the projected image to indicate that the location has not yet been sterilized. "NOT STERILIZED" is an illustrative example. Step 1704—The color camera 1612 captures a color video of the patient. The color video image is transferred from the color camera 1612 to the computer system, and optionally to remote computers system via the radio module 6. The computer system 1601, or the remote computers system, process the video images to confirm that the sterilization has occurred. As an embodiment, the confirmation process detects the reflectivity of the surface of the patient 10. The liquids that are used for sterilization can be visually detected base upon their shiny reflection as compared to the patient's skin. Alternatively, some sterilization liquids are colored, and therefore easily identified in the video stream. At Step 1704, after the sterilization has been confirmed progress made to Step 1705, wherein the warning message is turned off and the procedure performed at Step 1706.

As a further embodiment, the sterilization liquids can be infused with materials that fluoresce when receiving predetermined frequencies of light. In this embodiment, one of the IR light sources 1604 is configured to emit the frequency of light associated with the activating frequency of the material infused into the sterilization liquid. One of the IR cameras 1603 is configured to receive the emitted frequency. The IR video image is transferred from the IR camera 1603 to the computer system, and optionally to remote computers via the radio module 6. At Step 1704, the computer system 1601, or the remote computers, process the IR video image to confirm the presence of the infused fluorescing material.

As a further embodiment, at Step 1704, instead of utilizing a video image, the sound recorded by the microphone 1615 can be analyzed to determine whether the sterilization has occurred. Audio cues, such as for example, the ripping sound associated with opening the packaging of the sterilizer, and the sound generated by wiping the sterilizer on the patient's body, can be utilized.

When a user is utilizing a vein viewer device during a procedure, they are focusing their gaze primarily on the venipuncture location on the patient. In various embodiments herein, messages are to be displayed on the vein viewer, or projected by the projector 1602 in the vein viewer, or displayed on a companion device, such as, for example, a smart phone. Alternatively, referring to FIG. 16, the messages can be converted by the computer system 1601 and played over audibly by the speaker 1616. This will allow to user to receive the audible message while keeping their visual gaze on the patient. As a further embodiment, a haptic output device 1617, such as for example a vibrator, can receive messages from the computer system 1601 and provide haptic feedback to the user, once again enabling the user to keep their visual focus on the patient.

Figure 18:
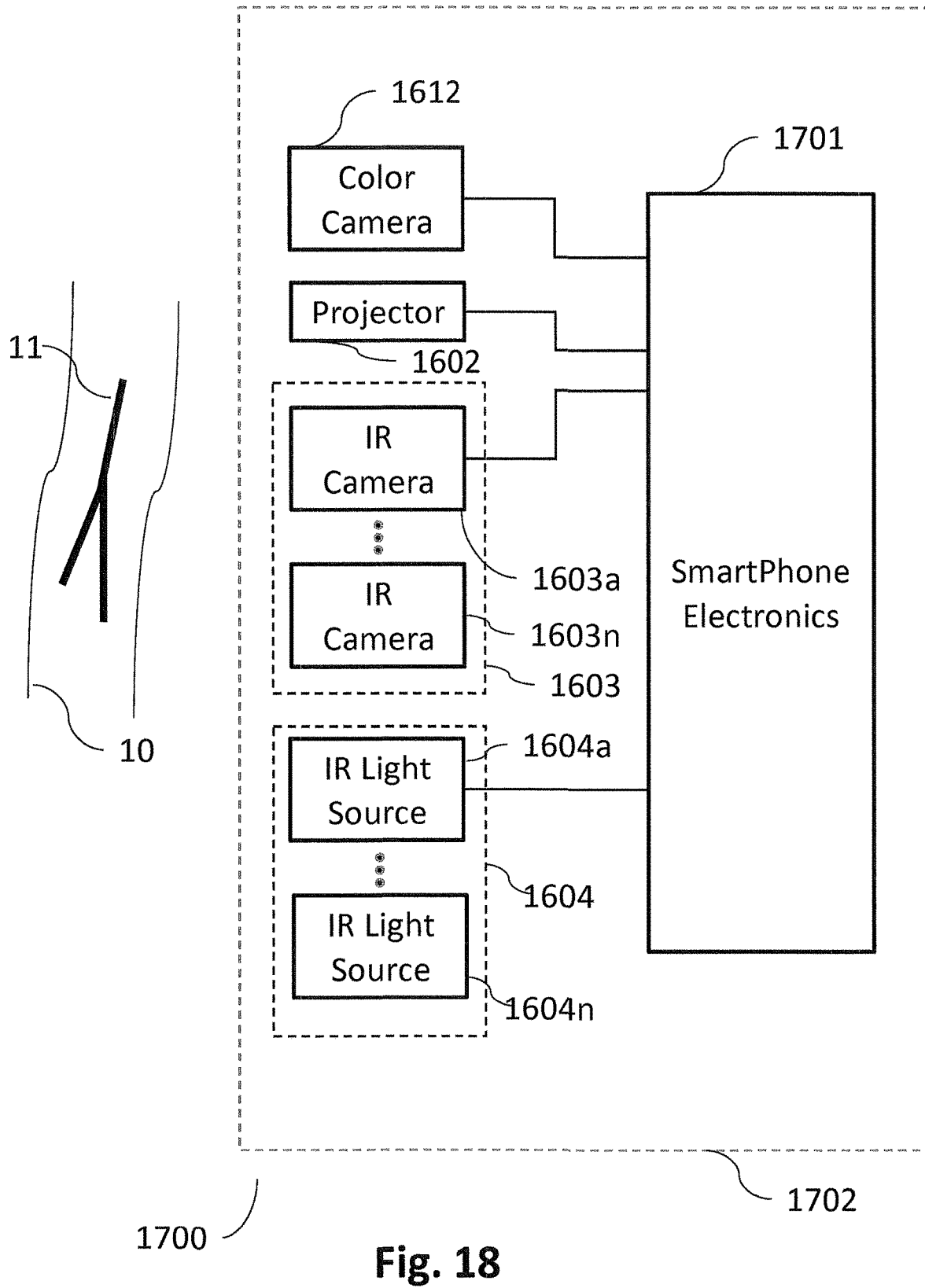
FIG. 18 illustrates a smartphone with an incorporated vein viewer.

FIG. 18 illustrates integrating the IR Light sources 1604, IR Cameras 1603, projector 1602, and optionally a color camera 1612 into the outer housing 1702 of a smartphone 1700. The IR camera 1603 and the projector 1602 can connect to the smartphone electronics 1701 through electrical interfaces, such as for example, industry standard interfaces such as USB. Alternatively, the IR camera 1603 and the projector 1602 can connect directly to the memory bus of the smartphone electronics 1701. The IR light source 1604 can be enabled by the smartphone electronics. The smartphone electronics 1701 performs the functionality described previous for the computer system 1601. Smartphones have a very rich set of input modalities, such as touch screens, fingerprint sensors, camera inputs, voice recognition, all of which can be utilized to operate the vein viewing capabilities of the device.

Figure 19A:
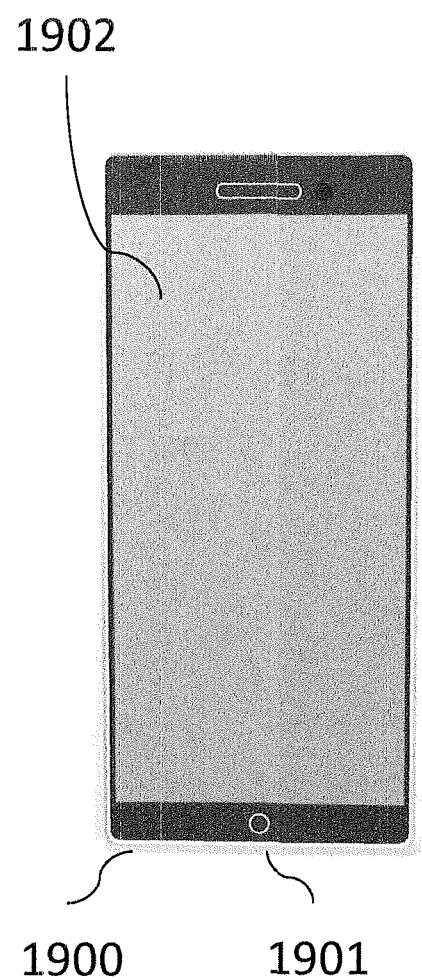
FIG. 19A illustrates a smart phone having a display and a bottom connector for electrical communications.
Figure 19B:
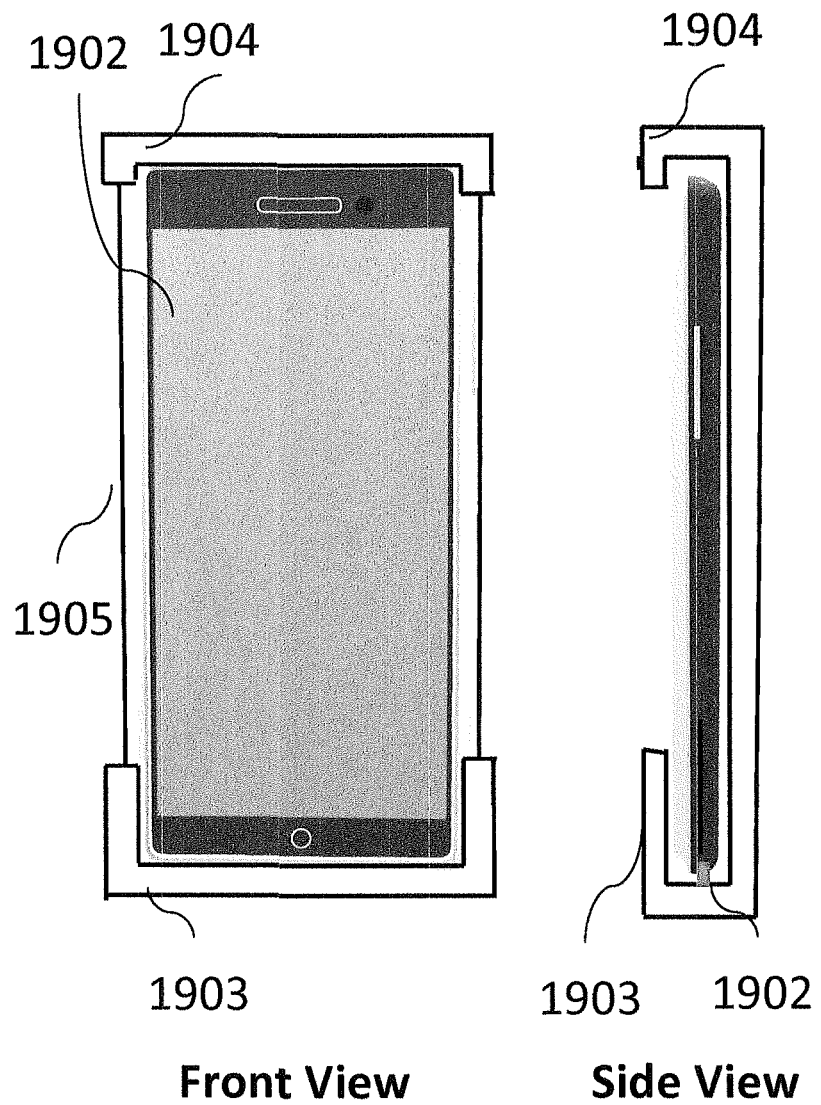
FIG. 19B shows a front and side view of a vein viewing attachment for connection to and communications with a smart phone.

FIG. 19A illustrates a smartphone 1900 having a touchscreen 1902 and a bottom connector 1901 through which the smartphone can be charged and through which data can be communicated to remote devices. Some phones utilized standard physical and electrical connectors, such as, for example android phones which utilize USB Micro-B connectors for both data transfer and charging, and the Apple iPhone which use an 8-pin Lightning connector. FIG. 19B shows a front view and a side view of a vein viewer accessory 1905 which mates to the smartphone 1900. The vein viewer accessory includes a connector 1902 which mates with the connector 1901 on the smartphone. Bottom walls 1903 and top walls 1904 mechanically hold the accessory 1905 in place relative to the smartphone 1900.

Figure 20:
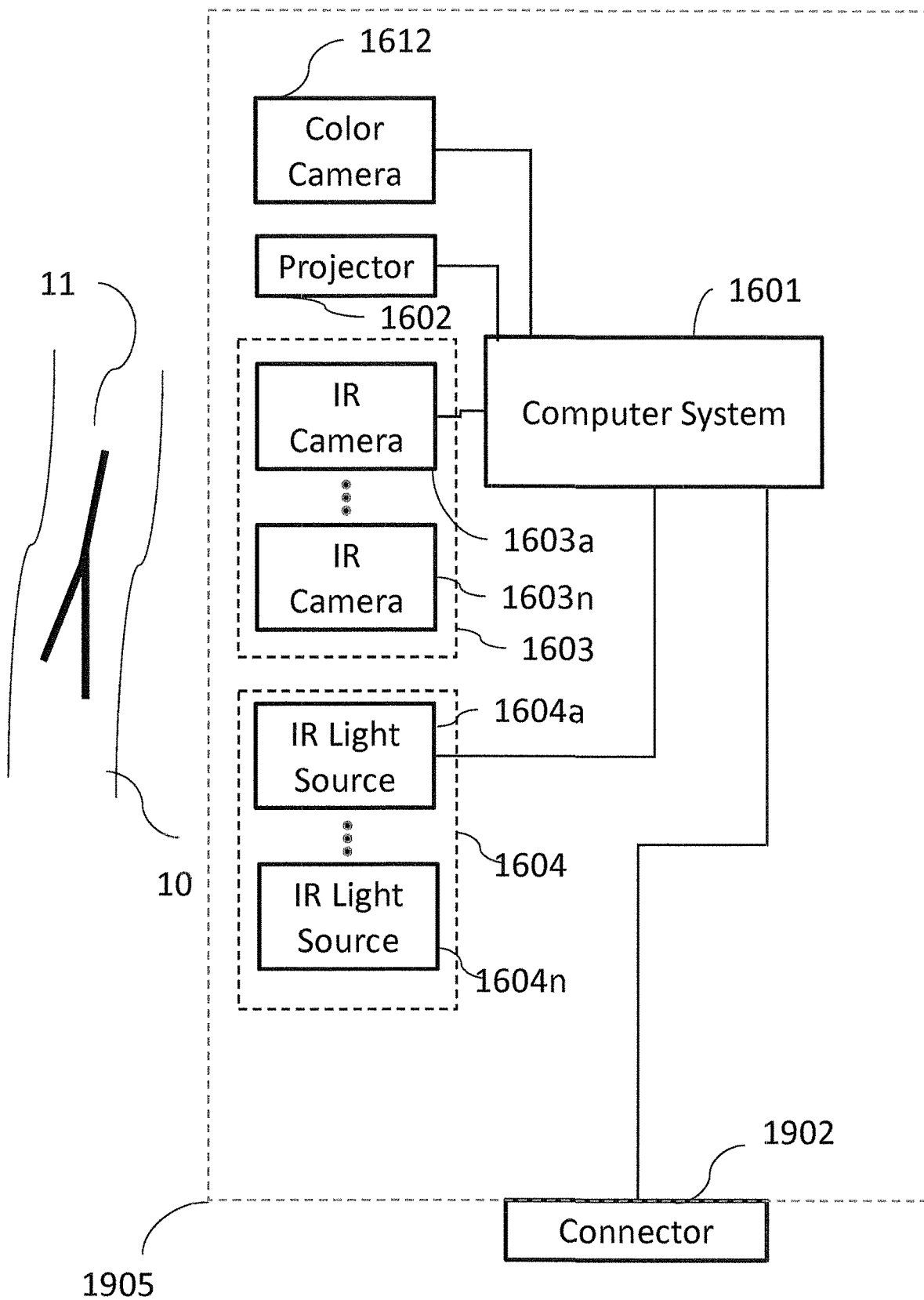
FIG. 20 is a block diagram of the vein viewer attachment of FIG. 19B.

FIG. 20 further illustrates the vein viewing accessory 1905 of FIG. 19B in greater detail. The connector connects to a computer system 1601 which in turn connects to one or more IR cameras 1603, one or more IR light sources 1604, the projector 1602 and optionally a color camera 1612. The operation of the computer system 1601 is the same a previously described herein, however, the input and display functionality previously integrated into the vein viewer is now handled by the touchscreen display 1902 of the smartphone 1900. The computer system 1601 sends display commands and information through the connector 1902 to the smartphone 1900, which in turn has programming or an application arranged to display the received information on the touchscreen display 1902. Conversely, the smartphone 1900 is programmed or has an application to receive touchscreen 1902 input and communicates the input information through connector 1901 to the computer system 1601. Accordingly, if a user already owns a smartphone, the incremental cost for vein viewing functionality is reduced in that the vein viewing accessory 1905 has fewer components than a stand-alone vein viewer, since the accessory does not need to incorporate a display or input keys. Still further, the vein viewing accessory can derive power from the smartphone 1900 through the connectors 1901 and 1902, and therefore does not need to incur the cost of a standalone battery, or power charging circuitry. Still further, the smartphone 1900 with the attached vein viewing attachment 1905 is multifunctional. In a first mode it can be utilized as a traditional smartphone and provide the user with traditional smartphone functionality, and in a second mode it can be utilized for displaying the vasculature of the patient.

Figure 21:
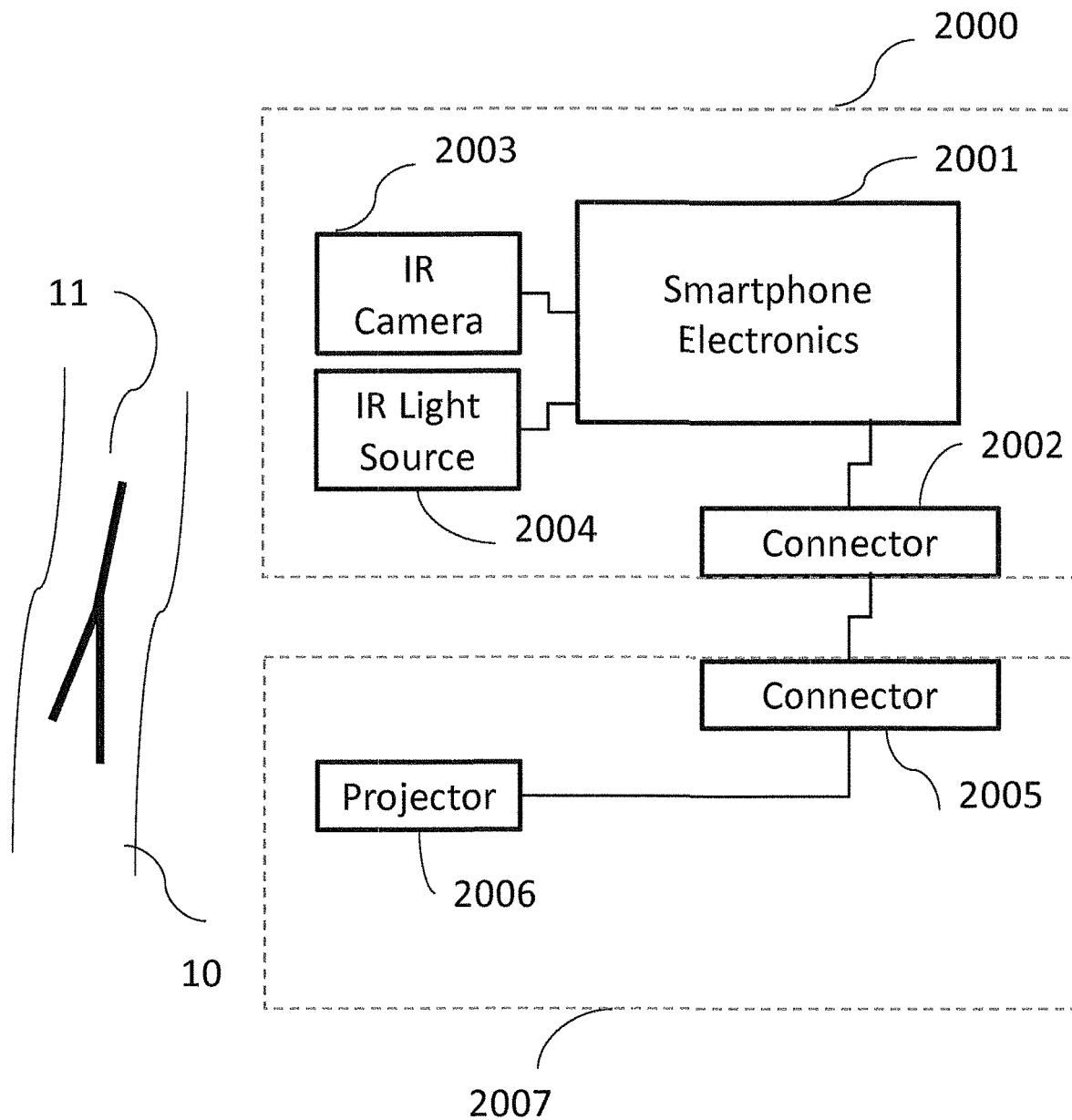
FIG. 21 is a block diagram of an embodiment of a vein viewer attachment for connecting to a smart phone.

FIG. 21 illustrates a further embodiment of the present invention, where the vein viewer accessory 2007 is greatly simplified. A projector 2006 communicates through connector 2005 to smartphone 2000. The vein viewer accessory can be housed in the same attachment housing shown in FIG. 19. There are known smartphones that have integrated IR light sources and IR cameras. In this embodiment, the smartphone 2000 has smartphone electronics 2001 which communicates through connector 2002 and connector 2005 to the projector 2006. The smartphone electronics 2001 connects to an IR lightsource 2003 and an IR camera 2004. When the smartphone 2000 is operating in a vein viewing mode, the smartphone electronics 2001 enables the IR light source 2004 which in turn projects IR light on the patient. The IR camera 2003 then receives the image of the patient and communicates the image to the smartphone electronics 2001. The smartphone electronics processes the image to extract the vein image 11 from the image captured by the IR camera 2003, and communicates the vein image through connectors 2002 and 2005 to the projector 2006. The projector 2006 then projected the vein image 11 onto the patent 10 in visible light.

For vein viewers to work appropriately, it is critical that the field of view of the IR camera 2003 and the field of view of the projector 2006 must be coaligned. If the field of views are not aligned, the projector 2006 would project an image that is offset from the actual vein locations. Such alignment has traditionally been done mechanically, however, in the case where the IR Camera 2003 is in the smartphone 2000, and the projector 2006 is in the accessory 2007, it is difficult if not impossible to mechanically align and fix the fields of view. As an embodiment of the present invention, the projector 2006 is configured to transmit two frequencies of light, a visible light to project the visible vein image, and an IR light representative of the vein image. The IR camera 2003 then receives an image that is composed of both the patients vein pattern and the IR projection of the vein image. This image is then analyzed by the smartphone electronics 2001. If the actual vein image received from the patient, and the IR vein image projected are coaligned, no adjustments are made. However, if they are misaligned, the smartphone electronics determines the magnitude and direction of misalignment and shifts accordingly the image signal sent to projector 2006. In this manner, the alignment is automatically electronically adjusted.

As an alternative embodiment, alignment can be electrically implemented with a projector 2006 that projects a single visible color of light to display the vein image, and an IR Camera 2003 that is arranged to receive both IR light and the visible color of light transmitted by the projector. In this embodiment the IR camera is configured so its view of view of the IR light and the visible light are aligned. The projector 2006 projects in visible light the vein pattern, and the IR camera captures the image of both the visible light pattern projected by the projector 2006 and the actual IR image of the vein pattern. This image is then analyzed by the smartphone electronics 2001. If the actual vein image received from the patient, and the visible vein image projected are coaligned, no adjustments are made. However, if they are misaligned, the smartphone electronics determines the magnitude and direction of misalignment and shifts accordingly the image signal sent to projector 2006. In this manner, the alignment is automatically electronically adjusted.

While the electronic adjustment has been described with reference to a smartphone and an attached vein viewer accessory, it is not intended to be so limited. The electronic adjustments described above can be implemented in any of the vein viewer embodiments previously described.

It is known in the art to utilize a virtual reality headset to distract a patient while an IV is inserted or blood is being drawn. The virtual reality headset connects to a smartphone which runs either a video or video games which is displayed on the virtual reality headset. The virtual reality headset contains a radio, such as 802.11 or Bluetooth, for receiving the video or video game signals from the smartphones. It is however cumbersome for a practitioner who is performing venipuncture to handle both a smartphone and a vein viewer at the same time.

As an embodiment of the present invention, referring to FIG. 4, the computer system 403 stores the video or the video game and is configured to transmit via the radio 402 the video or a video game to a wireless virtual reality headset (not shown). It is an object of the present invention to coordinate the timing of a video with the venipuncture. For example, it is desirable to coordinate the content of the video to ensure a particular segment is being played at the exact time the venipuncture is performed. For example, the video might have a segment wherein a video character has something that touches or pokes their arm at the exact time of the venipuncture. In one embodiment, the vein viewer can display a message (or provide an audible indication) to the user that the appropriate video scene is about to appear. As an alternative embodiment, the user of the vein viewer can provide and input to the vein viewer immediately before they are about to stick the patient, which in turn causes the computer system 403 to advance, or jump, the video to the appropriate scene. Alternatively, in the case of a video game, the user of the vein viewer can instruct the computer system 403 to run a particularly challenging portion of a video game at moment they are performing the venipuncture.

It is known that providing haptic stimulus to a patient can distract the patient from the venipuncture and make the procedure more pleasant. As an embodiment of the present invention, a radio enabled haptic device (not shown) having one or more vibrating buzzers can be strapped to the patient's body at a location remote from the venipuncture location. The radio could be, for example, an 802.11 radio or a Bluetooth radio. Referring to FIG. 4, the computer system 403 can send instructions to the haptic device to instruct the one or more vibrating buzzers to activate. They can be activated in interesting sequences, therefore distracting the patient. As a further embodiment, a wireless button, which can be operated by the patient, communicates key depressions to the vein viewer and the computer system can vary the haptic buzzers as a function of the key presses. This allows for the implementations of distracting games, such as, for example, a game where the buzzing pattern must be repeated by the patient.

As a further embodiment, haptic device can consist of both buzzers as well as multiple color lights. Further the wireless button can consist of multiple buttons. In this manner, even more complex games can be implement further distracting the patient. For example, the haptic device can have 4 different LED lights and the button can have for buttons, each having a corresponding color. The computer system 403 triggers a random pattern of the LED's, and the patient must repeat the pattern by pressing the corresponding buttons (the computer system 403 confirms the pattern). A further embodiment, 4 buzzers can be position in the same position as the 4 lights, for example, in a "X" pattern. The computer system 403 can instruct a sequence of buzzes and lights, which in turn the patient must repeat at a four button controller.

Still further, an embodiment with just a single buzzer and a two key remote can be controlled by the computer system 403. In this game, the computer system sequentially buzzes at two different frequencies. The patient has to determine which frequency is faster by pressing an up button or down button. The frequencies can get closer to each other thereby increasing the difficulty.

As a still further embodiment, the haptic device also contains a speaker for playing music streamed from the computer system 403. The computer system 403 can cause the haptic device to buzz in synchrony with the music. Still further, a segment of the music can be played, and the patient has to keep the beat via the remote button to the song to proceed.

While specific embodiment have been described game wherein a haptic device is controlled by the computer system 403, and a remote control communicates key depressed to the computer system 403, the invention is not limited to these embodiments. Many other games and distractions can be implemented with the computer system 403 contained within the vein viewer, the haptic device, and the remote control.

As a still further embodiment, the vein viewer can be utilized by a practitioner who then marks the desired location for venipuncture on the patient's skin. The vein view is then set into a mode wherein the computer system 403 causes the projector to project a cartoon or moving image, or a video game. The vein viewer is then handed to the patient who projects the image on a wall, tabletop or piece of paper. Alternative, when entering this mode, the vein viewer can remain in the stand but vein viewer is aimed at a wall for projecting the cartoon, moving image or video game on the wall.

There are often situations where a patient has to undergo repeated venous access procedures. For example, it is often the case where an infusion patient needs to go periodically, such as once a week, to an infusion center, wherein an IV is inserted into a vein. Another example is home infusion, wherein periodic IV access is often required. A still further example is a hospital patient who is in the hospital for an extended time period and requires multiple IVs. It is an embodiment of the present invention to capture procedure data, such as the patients name and/or identifying information, the name of the person performing the procedure, the procedure date/time and an image of the location of successful and/or unsuccessful IV attempts. The procedure data can be stored in the computer system 403 or in the remote computer system and can be retrieved when the patient comes back for a repeat procedure. It will be very helpful to the practitioner performing the venipuncture to see the history of which practitioner performed the procedure, which locations were successful, and which were unsuccessful. The retrieved information can be displayed a screen on the vein viewer or can be projected by the projector 2 onto the patient, or can be displayed on a radio connected companion device, such as for example, a smartphone, PDA, tablet, portable computer, fix computer, computer cart on a wheeled stand, or printed onto paper.

There are various ways to capture the practitioner and patient name and/or identifying information. The identifying information, such as for example, a practitioner and patient number, can be entered via a touchscreen on the vein viewer or a radio connected companion device. Further, the information can be contained in a barcoded wristband or ID card which is scanned and decoded by the vein viewer. Still further, the patient information can be entered via RFID or via biometrics, such as, for example, fingerprint entry, vein pattern, face recognition, or voice recognition.

Time of flight cameras are known which measure the distance to an object. In such systems, very short pulses of light are emitted and reflections off remote objects are received by a sensor. A timer measures the round-trip time for the light to travel from the camera to the object and then reflected back to the sensor. Since the speed of light is a constant, once the time of flight is known the actual distance can be calculated.

Figure 22:
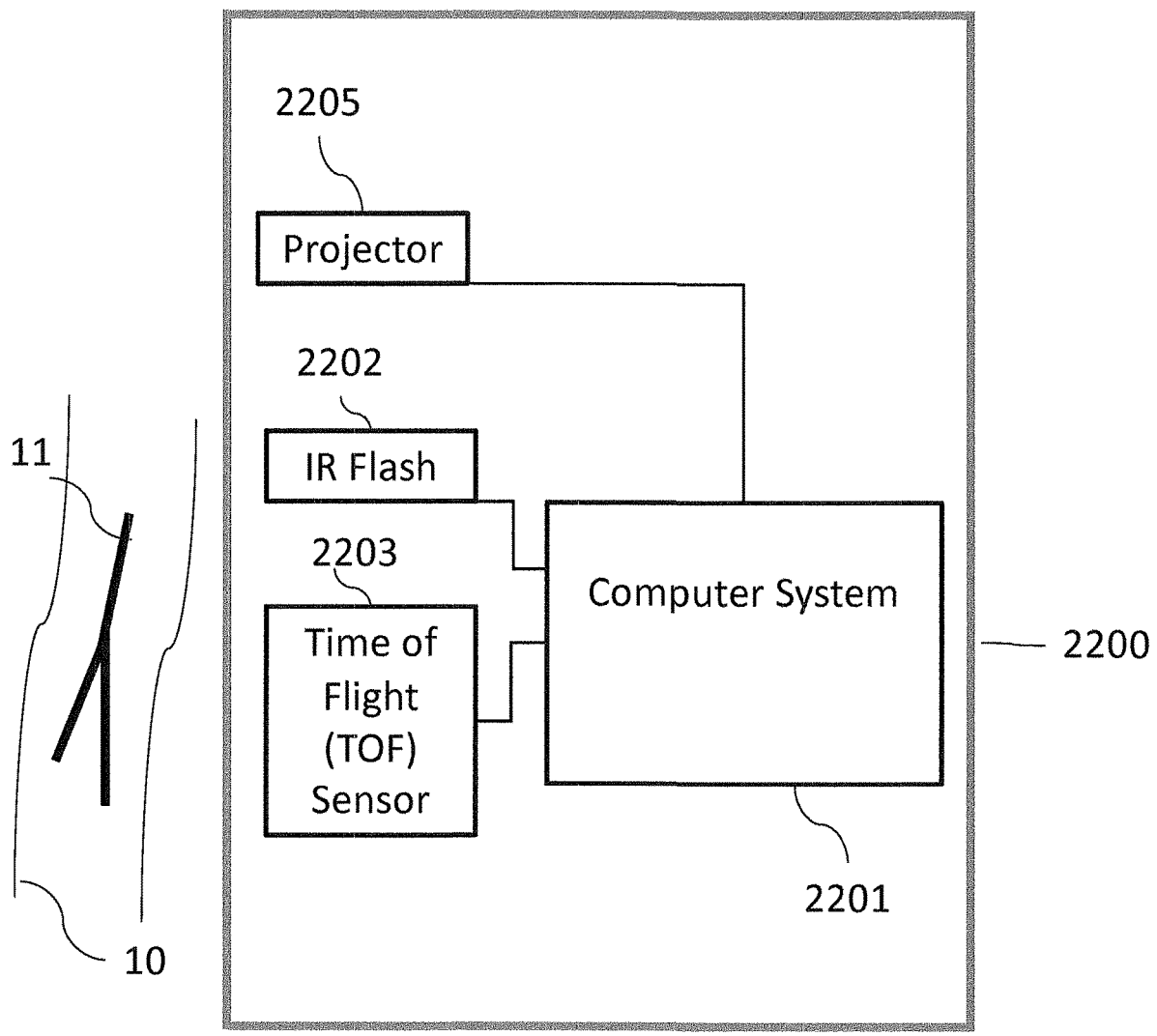
FIG. 22 is a block diagram of a time-of-flight vein viewing system.

FIG. 22 is an embodiment wherein a vein viewer 2200 utilizes time of flight calculations for determining the position of the vasculature 11 within a patient 10. The computer system 2201 instructs the IR flash 2202 to emit a very short light pulse of IR light that is aimed at a region of interest on a patient 10. As an example, the duration of this pulse can be in the range of 1 to 10n seconds. The time-of-flight (TOF) sensor 2203 includes a two-dimensional IR sensor imaging array having a field of view corresponding to the region of interest on the patient 10. The TOF sensor 2203 also includes timers for each of the individual sensors within sensor array. At the initiation of the IR pulse, the timers begin to count and they stop counting when receiving the IR light pulse reflected from the patient 10. Since it is known that human tissue is somewhat transparent to IR light, some of the reflected light is representative of the underlying structure, such as the vein pattern 11, of the patient. Accordingly, the reflected image received by the TOF sensor contains information related to the position and depth of the vein pattern 11. The received image, together with the depth information is then provided to the computer system 2201, which turn outputs the image to the projector 2204, which in turn projects a visible image of the vein pattern onto the patient 10. To represent the depth information, the projected vein pattern can be color coded, wherein various depth are represented by different colors. The invention is not intended to be limited to projecting color images to represent depth, as there are many other methods of representing depth in a two-dimensional image, such as for example, displaying numeric information in the projection, or projecting elevation lines as are done in elevation maps.

The invention has been described utilizing a flash TOF system with a two-dimensional sensor array, however, other types of TOF systems can be utilized. For example, there are vein viewing devices that scan a single laser beam in a two-dimensional pattern across a patient and utilize a single sensor for sensing the reflected light. As a further embodiment herein, such a scanned system can be modified to measure the distances to the vein pattern. In this embodiment, the projected laser is modulated so that it emits a short pulse, for example 1-10n seconds, at a rate corresponding to the number of samples obtained per image frame. For example, assuming an image of 640 by 480 samples, the laser with emit 640*480=307,200 short pulses for each frame. The sensor would have a timer that initiates timing at the start of each pulse and terminates upon receiving the reflected light. The resulting time is then converted to a distance measurement for that specific sample.

While many of the embodiments herein described IR cameras for detecting the vein patterns, the invention in not limited thereto. Other types of imaging approaches can be used for detecting the vascular, such as, for example, scanned lasers systems. Many of the embodiments herein described a projector for projecting a visible vein pattern. The projector can be any projector capable of projecting a visible image onto a patient, such as for example, a DLP projector, LCOS projector, an LCD projector, or a scanned laser projector.

In various embodiments, the term remote computer system or remote computer is used to describe a computer which is in radio communication with the vein viewer. However, the inventions herein are not so limited, and remote computer system and remote computer can refer to any device which is able to communicate directly or indirectly with the vein viewer. For example, servers, smartphones, PDAs, tablets, laptop computers, databases, access points, dedicated network appliances, cloud-based computers, IOT (internet of things) devices, can perform the function of the remote computer system.

Several embodiments herein utilized UVC light to sterilize the vein viewers. It is understood that other frequencies of light, such as for example, can be Far UV, can be utilized. Still further, while the sterilization chamber utilized light to sterilize the vein viewers, other know method of sterilization may be used.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments but should be defined only in accordance with the following claims and their equivalents.

What is claimed is:

1. A cleaning chamber for cleaning a vein viewing device, comprising:
   a housing comprising:
      an access door having an open position and a shut position, wherein when the access door is in the open position the vein viewing device can be placed inside the housing, and wherein when the access door is in the closed position the housing and access door together envelop the vein viewing device;
      a detector for detecting when the vein viewing device is contained within the housing;
      a light source contained within the housing arranged to illuminate the exterior surfaces of the vein viewing device, wherein the light source is disabled when the detector fails to detect the presence of the vein viewing within the housing.

2. The cleaning chamber according to claim 1, further comprising:
   a door position detector for detecting when the access door is in the closed position, wherein the light source is disabled when the door detector fails to detect the door is in the closed position.

3. The cleaning chamber according to claim 2, further comprising:
   a lock mechanism for locking the access door in the closed position,
   a timer for turning on the light source for a predetermined time, wherein the access door remains locked in the closed position until the light source is on for the predetermined time.

4. The cleaning chamber according to claim 3, further comprising:
   a user interface for manually unlocking the lock mechanism, wherein the user interface is responsive to unique unlocking data, wherein said unlocking data can be at least one of a unique key sequence or a unique biometric input.

5. The cleaning chamber according to claim 4, wherein said biometric input is at least one of a fingerprint, facial recognition, voice recognition, vein pattern recognition, or RFID input.

6. The cleaning chamber according to claim 1, further comprising:
   a portable stand having a positional arm;
   a mounting mechanism at the distal portion of the arm for removably receiving the vein viewing device;
   wherein the housing is affixed to the portable stand.

7. A portable vein viewing cleaning device for cleaning a vein viewing device, comprising:
   a housing comprising:
      an access door having an open position and a shut position, wherein when the access door is in the open position the vein viewing device can be placed inside the housing, and wherein when the access door is in the closed position the housing and access door together envelop the vein viewing device;
      a light source contained within the housing arranged to illuminate the exterior surfaces of the vein viewing device;
   a portable stand having a positional arm;
   a mounting mechanism at the distal portion of the positional arm for removably receiving the vein viewing device;
   wherein the housing is affixed to the portable stand.

8. The cleaning chamber according to claim 7, further comprising:
   a door position detector for detecting when the access door is in the closed position, wherein the light source is disabled when the door detector fails to detect the door is in the closed position.

9. The cleaning chamber according to claim 8, further comprising:
   a lock mechanism for locking the access door in the closed position,
   a timer for turning on the light source for a predetermined time, wherein, the access door remains locked in the closed position until the light source is on for the predetermined time.

10. The cleaning chamber according to claim 9, further comprising:
    a user interface for manually unlocking the lock mechanism, wherein the user interface is responsive to unique unlocking data, wherein said unlocking data can be at least one of a unique key sequence or a unique biometric input.

11. The cleaning chamber according to claim 10, wherein said biometric input is at least one of a fingerprint recognition, facial recognition, voice recognition, vein pattern recognition, or RFID input.

12. The cleaning chamber according to claim 7, wherein said light source emits UVC light.

13. The cleaning chamber according to claim 7, further comprising:
    a power supply within the housing for supplying power to the vein viewing device while the vein viewing device is positioned within the housing.

* * * * *